US012661648B2

(12) United States Patent
Eberwine et al.

(10) Patent No.: US 12,661,648 B2
(45) Date of Patent: Jun. 23, 2026

(54) HIGH THROUGHPUT MICROFLUIDIC DEVICE

(71) Applicant: THE TRUSTEES OF THE UNIVERSITY OF PENNSYLVANIA, Philadelphia, PA (US)

(72) Inventors: James Eberwine, Philadelphia, PA (US); Jai-Yoon Sul, Cherry Hill, NJ (US); Paulo Arratia, Philadelphia, PA (US); David Gagnon, Washington, DC (US); Ram Gona, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1423 days.

(21) Appl. No.: 16/968,230

(22) PCT Filed: Feb. 7, 2019

(86) PCT No.: PCT/US2019/017032
§ 371 (c)(1),
(2) Date: Aug. 7, 2020

(87) PCT Pub. No.: WO2019/157170
PCT Pub. Date: Aug. 15, 2019

(65) Prior Publication Data
US 2021/0031186 A1      Feb. 4, 2021

Related U.S. Application Data

(60) Provisional application No. 62/627,346, filed on Feb. 7, 2018.

(51) Int. Cl.
*B01L 3/00*          (2006.01)
*C12M 1/00*          (2006.01)
(Continued)

(52) U.S. Cl.
CPC ......... *B01L 3/50273* (2013.01); *C12M 23/12* (2013.01); *C12M 23/16* (2013.01);
(Continued)

(58) Field of Classification Search
CPC ......... B01L 3/50273; B01L 2200/0684; B01L 2300/0877; B01L 2400/0487; B01L 3/00;
(Continued)

(56) References Cited

U.S. PATENT DOCUMENTS 3,711,262 A     1/1973  Keck
5,034,506 A     7/1991  Summerton
(Continued)

FOREIGN PATENT DOCUMENTS

EP          2802417 A2     11/2014
JP       2001520377 A      10/2001
(Continued)

OTHER PUBLICATIONS

Ashburner M, Ball CA, Blake JA, Botstein D, Butler H, Cherry JM, Davis AP, Dolinski K, Dwight SS, Eppig JT, Harris MA, Hill DP, Issel-Tarver L, Kasarskis A, Lewis S, Matese JC, Richardson JE, Ringwald M, Rubin GM, Sherlock G. Gene ontology: tool for the unification of biology. The Gene Ontology Consortium. Nat Genet. May 2000;25(1):25-9.

(Continued)

*Primary Examiner* — Samuel P Siefke
(74) *Attorney, Agent, or Firm* — Riverside Law LLP

(57)          ABSTRACT

The present invention provides microfluidic devices capable of generating a flow of fluids within a chamber. The flow of fluids mix within the chamber to form a gradient of concentrations. The chamber is capable of accepting a cell culture and is accessible to retrieve the cell culture. The microfluidic devices are compatible with standard laboratory microscopes for optical analyses of the chamber.

11 Claims, 10 Drawing Sheets

(51) Int. Cl.
      *C12M 1/12*          (2006.01)
      *C12M 1/32*          (2006.01)
      *C12M 3/06*          (2006.01)

(52) U.S. Cl.
      CPC ............ *C12M 23/22* (2013.01); *C12M 25/14*
             (2013.01); *B01L 2200/0684* (2013.01); *B01L*
                   *2300/0877* (2013.01); *B01L 2400/0487*
                                                      (2013.01)

(58) Field of Classification Search
      CPC ...... C12M 23/12; C12M 23/16; C12M 23/22;
                                                C12M 25/14
      See application file for complete search history.

(56)                  References Cited

U.S. PATENT DOCUMENTS

| | | | |
|---|---|---|---|
| 5,350,674 | A | 9/1994 | Boenisch |
| 5,585,362 | A | 12/1996 | Wilson |
| 6,827,906 | B1 | 12/2004 | Bjoernson |
| 6,973,245 | B2 | 12/2005 | Bocanegra |
| 9,157,066 | B2 | 10/2015 | Eberwine |
| 9,845,480 | B2 | 12/2017 | Eberwine |
| 10,583,204 | B2 | 3/2020 | Eberwine |
| 10,646,590 | B2 | 5/2020 | Eberwine |
| 10,647,960 | B2 | 5/2020 | Eberwine |
| 10,883,082 | B2 | 1/2021 | Eberwine |
| 2002/0185183 | A1 | 12/2002 | O'Connor |
| 2005/0070018 | A1 | 3/2005 | Johnson |
| 2006/0215155 | A1 | 9/2006 | Weber |
| 2007/0166199 | A1* | 7/2007 | Zhou ................ B01L 3/502738 |
| | | | 422/400 |
| 2009/0311737 | A1 | 12/2009 | Locascio |
| 2013/0236376 | A1 | 9/2013 | Augstein |
| 2014/0057311 | A1 | 2/2014 | Kamm |
| 2014/0308178 | A1 | 10/2014 | Woudenberg |
| 2015/0321194 | A1 | 11/2015 | Weibel |
| 2017/0022464 | A1 | 1/2017 | Novak |
| 2017/0372927 | A1 | 12/2017 | Schuele |
| 2018/0016535 | A1 | 1/2018 | Levner |

FOREIGN PATENT DOCUMENTS

| | | |
|---|---|---|
| JP | 2004151109 A | 5/2004 |
| JP | 2005517399 A | 6/2005 |
| JP | 2005533636 A | 11/2005 |
| JP | 2013538582 A | 10/2013 |
| JP | 2015510111 A | 4/2015 |
| JP | 2017504320 A | 2/2017 |
| JP | 2017519996 A | 7/2017 |
| WO | 0175164 A2 | 10/2001 |
| WO | 2007084228 | 7/2007 |
| WO | 2011002957 A2 | 1/2011 |
| WO | 2011002957 A3 | 8/2011 |
| WO | 2013106458 A2 | 7/2013 |
| WO | 2013106458 A3 | 11/2013 |
| WO | 2017091718 | 6/2017 |

OTHER PUBLICATIONS

Beaucage et al., Tetrahedron Lett. 22:1859-1862 (1981) "Deoxynucleoside phosphoramidites—A new class of key intermediates for deoxypolynucleotide synthesis".
Chung BG, Choo J. Microfluidic Gradient Platforms for Controlling Cellular Behavior. Electrophoresis 2010, 31, 3014-3027.
Cooksey et al., Lab On A Chip 2009; 9(3):417-426 (2009) "A multi-purpose microfluidic perfusion system with combinatorial choice of inputs, mixtures, gradient patterns, and flow rates".
Donald R. Needham-VanDevanter, Laurence H. Hurley, Vincent L. Reynolds, Nicole Y. Theriault, Williams C. Krueger, Wendall Wierenga, Characterization of an adduct between CC-1065 and a defined oligodeoxynucleotide duplex, Nucleic Acids Research, vol. 12, Issue 15, Aug. 10, 1984, pp. 6159-6168.
Eberwine et al., "Analysis of gene expression in single live neurons" Proc Natl Acad Sci U S A 1992, 89, 3010-3014.
Geng T, Chang L. Microfluidic Electroporation for Cellular Analysis and Delivery. Lab Chip, 2013, 13, 3803.
Hansen et al., "high-throughput microfluidics to control and measure signaling dynamics in single yeast cells" Nature protocols 10.8 (2015): 1181-1197.
Herberholz J, Antonsen BL, Edwards DH. A lateral excitatory network in the escape circuit of crayfish. J Neurosci. Oct. 15, 2002;22(20):9078-85.
Huang TJ, Adcock IM, Chung KF. A novel transcription factor inhibitor, SP100030, inhibits cytokine gene expression, but not airway eosinophilia or hyperresponsiveness in sensitized and allergen-exposed rat. Br J Pharmacol. Nov. 2001;134(5):1029-36.
Kacharmina JE, Job C, Crino P, Eberwine J. Stimulation of glutamate receptor protein synthesis and membrane insertion within isolated neuronal dendrites. Proc Natl Acad Sci U S A. Oct. 10, 2000;97(21):11545-50.
Martinez J, Patkaniowska A, Urlaub H, Luhrmann R, Tuschl T. Single-stranded antisense siRNAs guide target RNA cleavage in RNAi. Cell. Sep. 6, 2002;110(5):563-74.
Maxam AM, Gilbert W. Sequencing end-labeled DNA with base-specific chemical cleavages. Methods Enzymol. 1980;65(1):499-560.
Mohanty, S.K., Sharma, M. & Gupta, P.K. Laser-assisted microinjection into targeted animal cells. Biotechnology Letters 25, 895-899 (2003).
Mumtaz, Ghosh, et al., "Design of liposomes for circumventing the reticuloendothelial cells" Glycobiology 1991, 1,5,505-510.
Nielsen PE, Egholm M, Berg RH, Buchardt O. Sequence-selective recognition of DNA by strand displacement with a thymine-substituted polyamide. Science. Dec. 6, 1991;254(5037):1497-500.
Ningsih, Z, et al. A Microfluidic Device for Spatiotemporal Delivery of Stimuli to Cells. AIMS Biophysics Mar. 2015; 2(2):58-72.
Palumbo G, Caruso M, Crescenzi E, Tecce MF, Roberti G, Colasanti A. Targeted gene transfer in eucaryotic cells by dye-assisted laser optoporation. J Photochem Photobiol B. Oct. 1996;36(1):41-6.
Paterson L, Agate B, Comrie M, Ferguson R, Lake T, Morris J, Carruthers A, Brown CT, Sibbett W, Bryant P, Gunn-Moore F, Riches A, Dholakia K. Photoporation and cell transfection using a violet diode laser. Opt Express. Jan. 24, 2005;13(2):595-600.
Pearson JD, et al. High-performance anion-exchange chromatography of oligonucleotides. Journal of Chromatography A. vol. 255, Jan. 21, 1983, pp. 137-149.
Schneckenburger H, Hendinger A, Sailer R, Strauss WS, Schmitt M. Laser-assisted optoporation of single cells. J Biomed Opt. Jul. 2002;7(3):410-6.
Shirahata Y, Ohkohchi N, Itagak H, Satomi S. New technique for gene transfection using laser irradiation. J Investig Med. Mar. 2001;49(2):184-90.
Soughayer JS, Krasieva T, Jacobson SC, Ramsey JM, Tromberg BJ, Allbritton NL. Characterization of cellular optoporation with distance. Anal Chem. Mar. 15, 2000;72(6):1342-7.
Tirlapur UK, Konig K. Femtosecond near-infrared laser pulses as a versatile non-invasive tool for intra-tissue nanoprocessing in plants without compromising viability. Plant J. Aug. 2002;31(3):365-74.
Tirlapur UK, König K. Targeted transfection by femtosecond laser. Nature. Jul. 18, 2002;418(6895):290-1.
Van Gelder RN, von Zastrow ME, Yool A, Dement WC, Barchas JD, Eberwine JH. Amplified RNA synthesized from limited quantities of heterogeneous cDNA. Proc Natl Acad Sci U S A. Mar. 1990;87(5):1663-7.
Zeira E, Manevitch A, Khatchatouriants A, Pappo O, Hyam E, Darash-Yahana M, Tavor E, Honigman A, Lewis A, Galun E. Femtosecond infrared laser-an efficient and safe in vivo gene delivery system for prolonged expression. Mol Ther. Aug. 2003;8(2):342-50.
International Search Report and Written Opinion issued in PCT/US19/17032, dated Jun. 20, 2019, 11 pages.

* cited by examiner

60

50

40

30

20

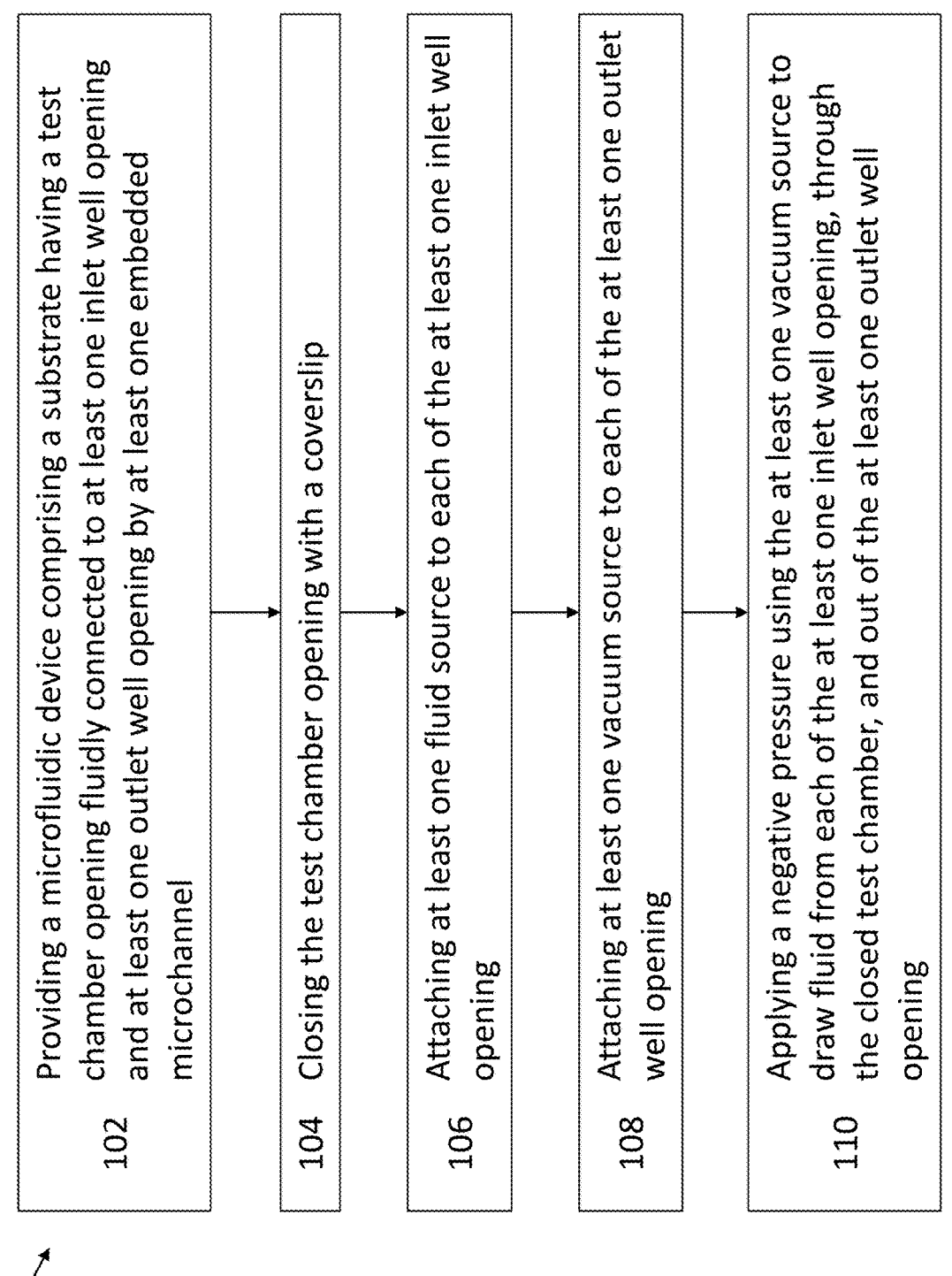

100

102  Providing a microfluidic device comprising a substrate having a test chamber opening fluidly connected to at least one inlet well opening and at least one outlet well opening by at least one embedded microchannel 104  Closing the test chamber opening with a coverslip 106  Attaching at least one fluid source to each of the at least one inlet well opening 108  Attaching at least one vacuum source to each of the at least one outlet well opening 110  Applying a negative pressure using the at least one vacuum source to draw fluid from each of the at least one inlet well opening, through the closed test chamber, and out of the at least one outlet well opening

Fig. 8

HIGH THROUGHPUT MICROFLUIDIC DEVICE

CROSS-REFERENCE TO RELATED APPLICATIONS

This application is a U.S. national phase application filed under 35 U.S.C. § 371 claiming benefit to International Patent Application No. PCT/US2019/017032, filed Feb. 7, 2019, which is entitled to priority under 35 U.S.C. § 119 (e) to U.S. Provisional Patent Application No. 62/627,346, filed Feb. 7, 2018, each of which applications is hereby incorporated herein by reference in its entirety.

BACKGROUND OF THE INVENTION

Microfluidic based devices act as tools that provide a miniaturized high-throughput functional platform for analysis of several chemical and biological species. These devices are employed in applications ranging from qPCR and sequencing of nucleic acids to the transfection of cells and the like. Certain microfluidic based devices are capable of generating gradients of desired concentration of fluids in a chamber or cell. However, no existing devices have been described to be compatible with standard laboratory microscopes and to be adequate for transcriptome induced phenotype remodeling, which requires the efficient transfection of a large number cells in varied microenvironments with a large range of RNA concentrations.

Therefore, there is a need for improved gradient generating microfluidic devices. The present invention addresses this need.

SUMMARY OF THE INVENTION

In one aspect, the present invention provides a microfluidic device comprising: a first layer having a top and bottom surface, a thickness in-between, and a plurality of wells and a test chamber embedded in the top surface, each of the wells being fluidly connected to the test chamber by a microchannel; a second layer having a top and bottom surface, a thickness in-between, and a plurality of well openings extending between the top and bottom surface; wherein the second layer is attachable to the top surface of the first layer such that each of the well openings of the second layer align with each of the wells of the first layer.

In one embodiment, the second layer further comprises; a test chamber opening extending between the top and bottom surface, the test chamber opening being in alignment with the test chamber of the first layer; and an indentation embedded in the top surface forming a perimeter around the test chamber opening, the indentation comprising an aperture that extends through to the bottom surface of the second layer. In one embodiment, the aperture is in alignment with a microchannel in the first layer connectable to a vacuum source. In one embodiment, the device further comprises a coverslip sized to cover the indentation and the test chamber opening of the second layer. In one embodiment, the device further comprises a third layer having a top and bottom surface, a thickness in-between, a plurality of well openings extending between the top and bottom surface, and a window opening extending between the top and bottom surface, wherein the third layer is attachable to the top surface of the third layer such that each of the well openings of the third layer align with each of the well openings of the second layer, and the window opening surrounds the indentation of the second layer.

In one embodiment, the device further comprises a support layer attached to the bottom surface of the first layer. In one embodiment, the first layer and the second layer each have at least two alignment slots that extend through top and bottom surfaces of each layer, each alignment slot being sized to accept a guide rod. In one embodiment, the alignment slots are positioned such that passing the alignment slots of the second layer over guide rods inserted into the alignment slots of the first layer aligns each well opening of the second layer with each well of the first layer. In one embodiment, the device further comprises one or more bubble traps or degassing valves connected to the microchannels, the test chamber, or both.

In another aspect, the present invention provides a method of generating a flow of fluids having a gradient of concentration, comprising the steps of: providing a microfluidic device comprising a substrate having a test chamber opening fluidly connected to at least one inlet well opening and at least one outlet well opening by at least one embedded microchannel; closing the test chamber opening with a coverslip; attaching at least one fluid source to each of the at least one inlet well opening; attaching at least one vacuum source to each of the at least one outlet well opening; and applying a negative pressure using the at least one vacuum source to draw fluid from each of the at least one inlet well opening, through the closed test chamber, and out of the at least one outlet well opening.

In another aspect, the present invention provides a method of administering a gradient of one or more agents to a population of cells, comprising the steps of: providing a microfluidic device comprising a test chamber and a plurality of wells, wherein the plurality of wells are fluidly connected to the test chamber by a plurality of microchannels; providing a cell culture substrate coated with a population of cells; contacting the cell culture substrate to the test chamber; administering a fluid medium comprising one or more agents to at least one of the plurality of wells; flowing the fluid medium from the at least one well to the test chamber, thereby generating a gradient of the one or more agents to the population of cells. In one embodiment, the one or more agents comprise at least one agent selected from the group consisting of a nucleic acid molecule, a protein, a peptide, and a small molecule. In one embodiment, the amount of the one or more agent to which each cell in the cell population is exposed to is dependent on the position of the cell in the test chamber.

In another aspect, the present invention provides a method of evaluating the effect of one or more agents on the ability to effectuate phenotypic change in a cell, comprising: providing a microfluidic device comprising a test chamber and a plurality of wells, wherein the plurality of wells are fluidly connected to the test chamber by a plurality of microchannels; providing a cell culture substrate coated with a population of cells; contacting the cell culture substrate to the test chamber; administering a fluid medium comprising one or more agents to at least one of the plurality of wells; flowing the fluid medium from the at least one well to the test chamber, thereby generating a gradient of the one or more agents to the population of cells and identifying one or more cells that exhibit a change in phenotype.

In one embodiment, the one or more agents comprise at least one agent selected from the group consisting of a nucleic acid molecule, a protein, a peptide, and a small molecule. In one embodiment, the one or more agents comprise an RNA molecule selected from the group consisting of: mRNA, ncRNA, microRNA, hnRNA, total RNA, non-coding RNA, siRNA, shRNA, and antisense RNA. In one embodiment, the RNA molecule is of a donor cell, and wherein the method comprises identifying one or more cells that exhibit a change in phenotype indicative of the donor cell. In one embodiment, the change in phenotype comprises a change in at least one phenotypic characteristic selected from the group consisting of gene expression, protein expression, immunological markers, morphology, physiology, synthesis of bioproducts, and membrane lipid composition. In one embodiment, the population of cells comprise a cell selected from the group consisting of: epithelial cells, astrocytes, neurons, fibroblasts, cardiomyocytes, embryonic fibroblasts, keratinocytes, adult stem cells, embryonic stem cells, and induced pluripotent stem cells.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 6A depicts a schematic of microchannels for a 2D diffusor. This arrangement provides flexibility for the simultaneous testing of four species at various concentrations, which are produced by diffusion within the device. FIG. 6B depicts exemplary microfluidic channels during testing.

FIG. 8 is a flowchart of an exemplary method of using a microfluidic device of the present invention.

FIG. 9A depicts a simulation of RNA concentration profile to validate numerical solver and to model the time-response of the microfluidic device. FIG. 9B depicts the prediction of the concentration profile in an actual device. FIG. 9C depicts an experimental test run of fluid in the microfluidic device.

DETAILED DESCRIPTION

Figure 1:
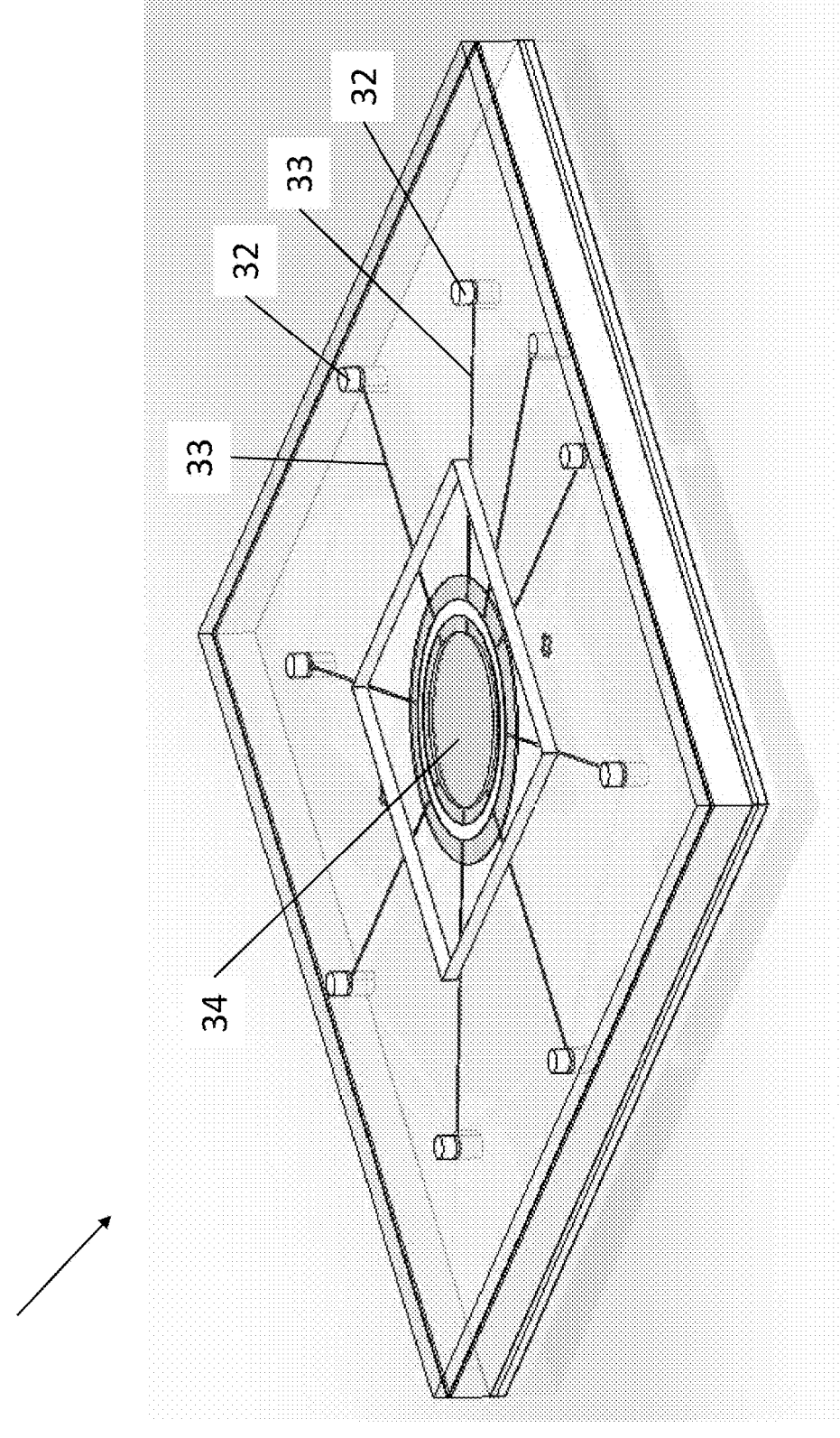
FIG. 1 depicts an exemplary microfluidic device.

The present invention provides microfluidic devices capable of generating a flow of fluids within a chamber. The flow of fluids mix within the chamber to form a gradient of concentrations. The chamber is an accessible cell culture chamber, suitable for the culture of dispersed cells or 3-D tissue sections. The microfluidic devices are compatible with standard laboratory microscopes for optical analyses of the chamber.

In one aspect, the present invention provides a method of administering a gradient of one or more agents to a population of cells. For example, in certain embodiments, the invention provides a high-throughput method of examining the effect of one or more agents on a population of cells, whereby each cell is exposed to a defined concentration of the one or more agents. For example, the device of the present invention can be used to deliver a gradient of one or more agents to the culture chamber, such that a cell is exposed to a defined concentration of the one or more agents, based upon its position in the cell culture chamber. In some embodiments, the gradient of agents delivered by way of the device allows each cell to be exposed to a unique recipe of agents, defined by the identity and amount of one or more agents. Exemplary agents include, but is not limited to, nucleic acid molecules, DNA, RNA, peptides, proteins, small molecules, dyes, hormones, vitamins, growth factors, stem cell factors, and the like.

In one embodiment, the present invention provides a method of evaluating phenotype conversion in a population of cells. For example, in one embodiment, the method comprises administering a gradient of one or more agents to the population of cells and determining which cells of the population altered its phenotype in response to the administered gradient. In certain embodiments, the method comprises administering a gradient of one or more nucleic acid molecules to the population of cells, thereby transfecting one or more cells of the population of cells with a defined recipe of nucleic acid molecules, as defined by the identity and concentration of each nucleic acid molecule. In certain embodiments, the method comprises determining which cell or cells of the population displayed characteristics of a change in phenotype in response to the administered gradient, thereby allowing for the determination of the identity and concentration of agent required for phenotype conversion.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Microfluidic Devices

Figure 2:
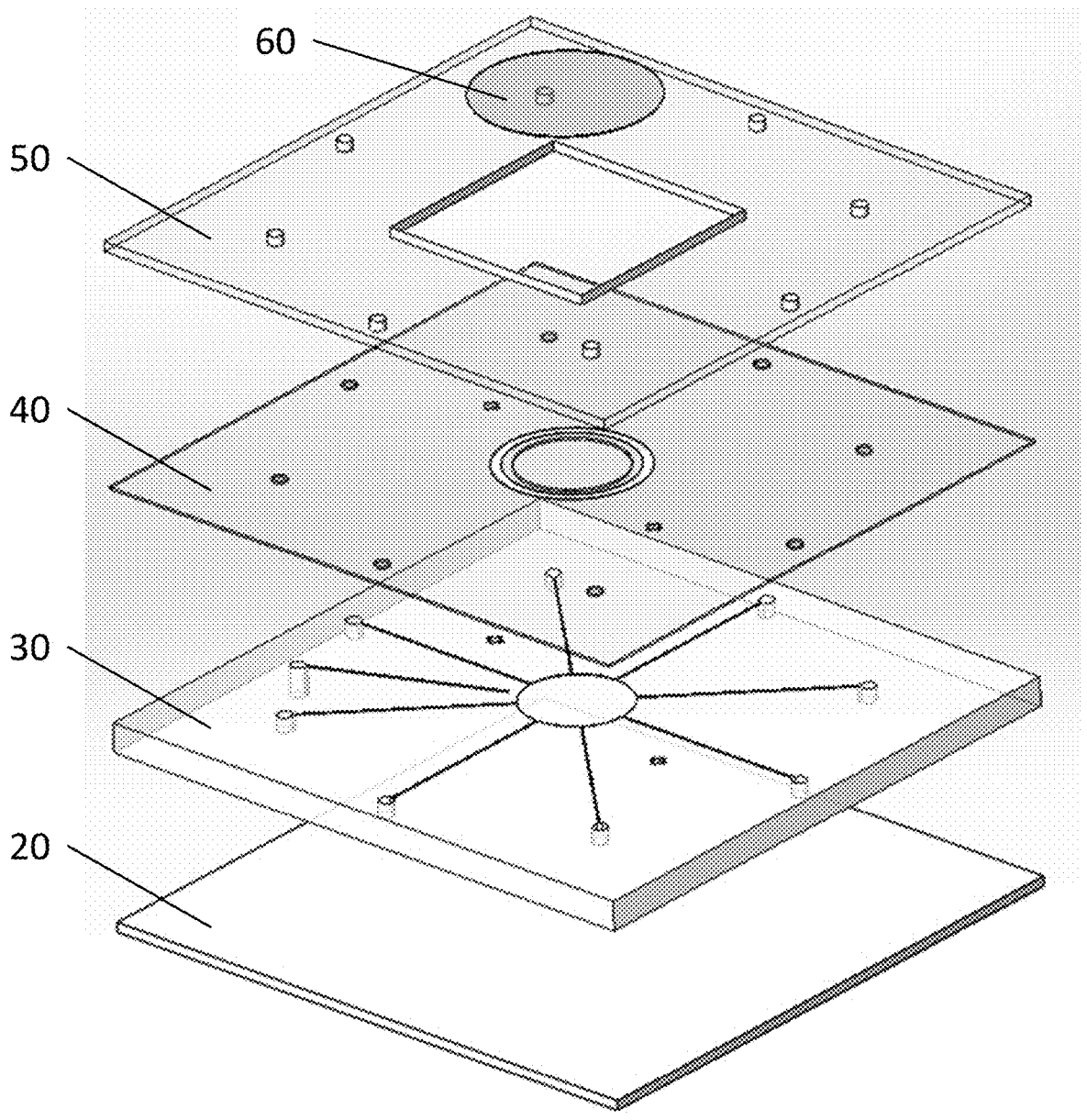
FIG. 2 depicts an exploded view of an exemplary microfluidic device, exposing the various layers of the device.

Referring now to FIG. 1, an exemplary microfluidic device 10 is depicted. Device 10 comprises a layered construction with a plurality of wells 32, each well 32 being fluidly connected to a test chamber 34 by a microchannel 33. An exploded view of the layered construction is depicted in FIG. 2, wherein device 10 comprises microchannel layer 30, cover layer 40, upper support layer 50, and coverslip 60. In various embodiments, device 10 comprises lower support layer 20, a substantially planar and rigid sheet of material providing structural support to device 10 and an anchoring platform for microchannel layer 30. In some embodiments, lower support layer 20 has a Shore hardness of between about 70D and 80D. In one embodiment, the lower support layer 20 has a Shore hardness of 75D.

Figure 3A:
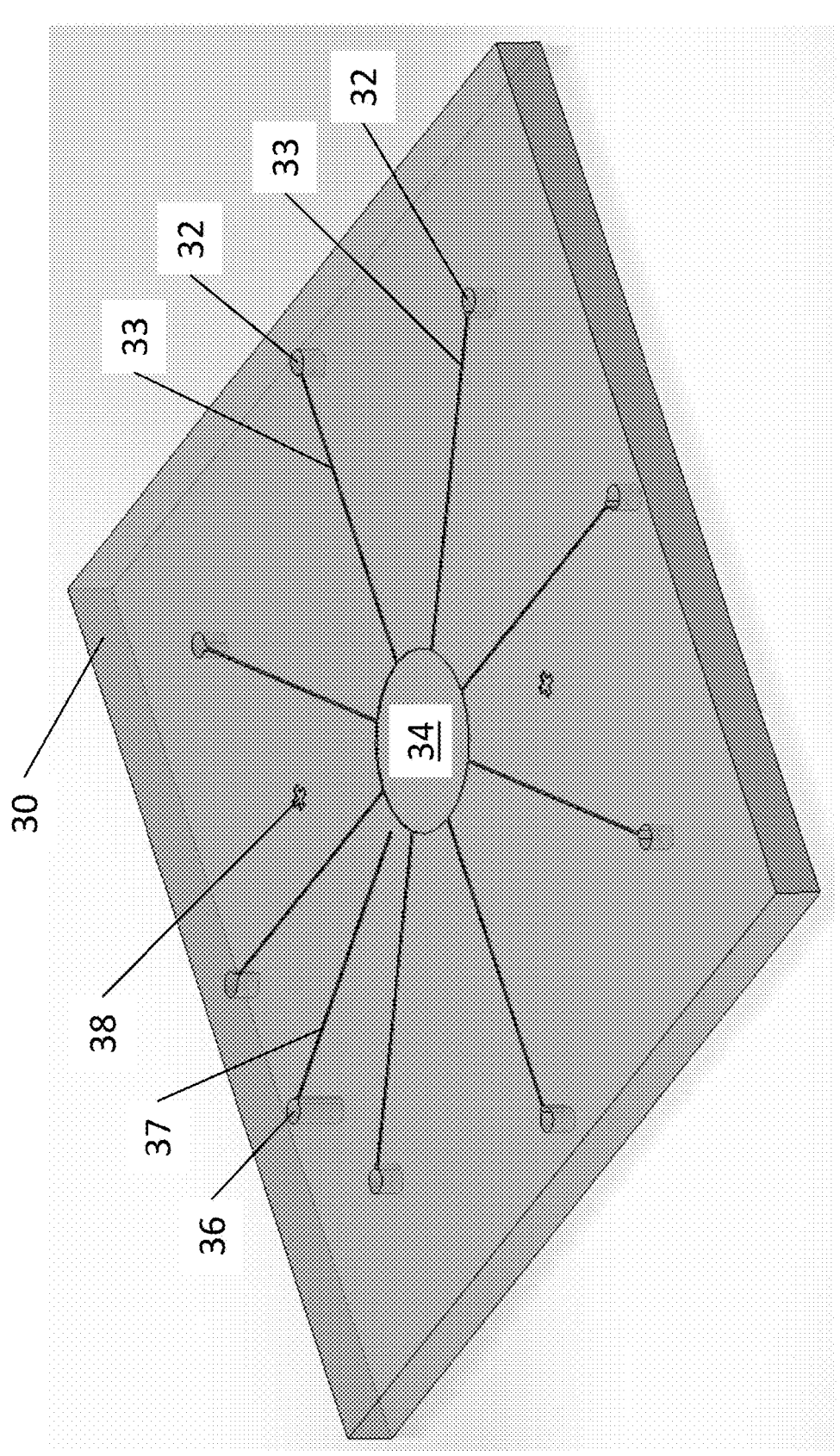
FIG. 3A depicts the microchannel layer of an exemplary microfluidic device.
Figure 3B:
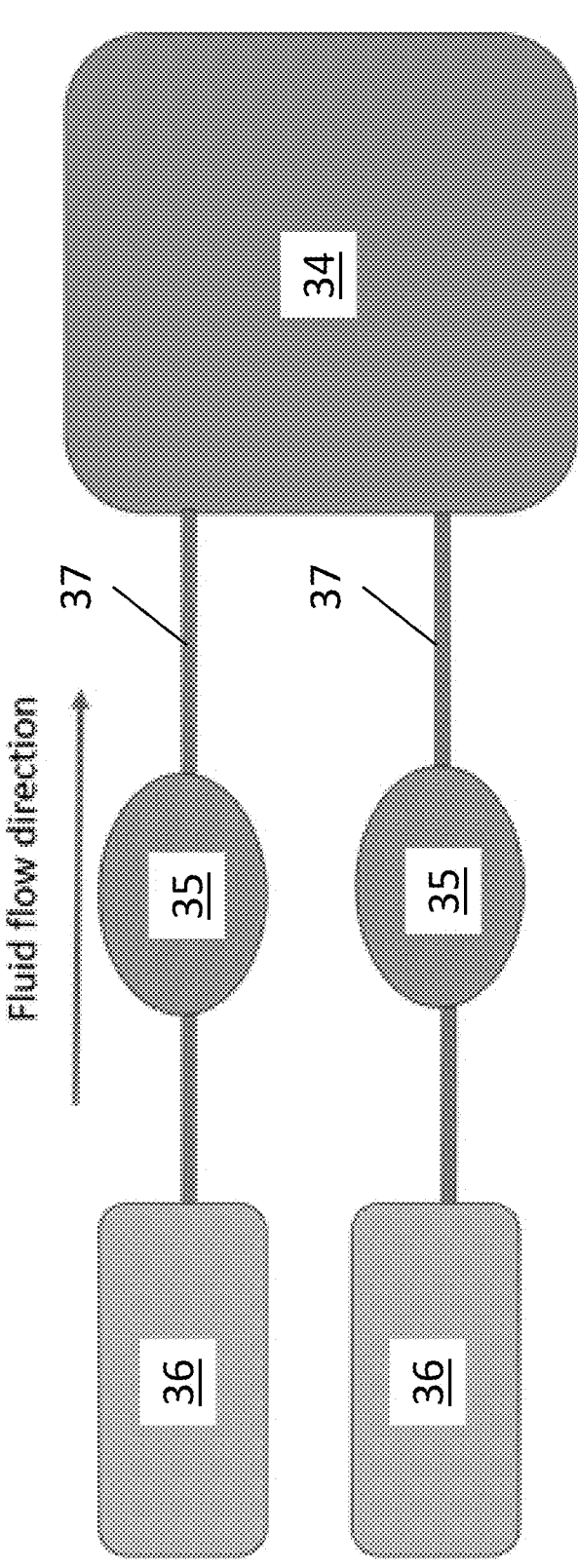
FIG. 3B depicts a schematic of an exemplary microfluidic device further comprising degassing valves.

Referring now to FIG. 3A, an exemplary microchannel layer 30 is depicted. Microchannel layer 30 has a substantially planar shape with a top surface, a bottom surface, and a thickness in-between. Microchannel layer 30 can have any suitable dimensions, such as a length and a width between about 5 and 15 cm, and a thickness between about 1 and 10 mm. Microchannel layer 30 comprises a plurality of wells 32, a test chamber 34, and a plurality of microchannels 33 embedded in the top surface fluidly connecting each well 32 with test chamber 34. Wells 32, test chamber 34, and the plurality of microchannels 33 can have any suitable dimensions. In various embodiments, wells 32 can have a diameter of between about 0.5 and 2.5 mm and a depth of between about 0.5 and 5 mm, test chamber 34 can have a diameter of between about 5 and 20 mm and a depth of between about 0.1 and 0.5 mm, and the plurality of microchannels 33 can each have a width and a depth of between about 0.1 and 0.5 mm. While FIG. 3A depicts 8 wells 32 arranged radially around test chamber 34, it should be understood that there is no limit to the number of wells 32 that microchannel layer 30 can have, and that each of the wells 32 and microchannels 33 can be arranged in any suitable configuration. In various embodiments, microchannels 33 and test chamber 34 may further comprise physical features that direct or influence the flow of fluid, such as uneven surfaces or etched patterns or protrusions. In some embodiments, microchannels 33, test chambers 34, or both are fluidly connected to one or more bubble traps 35 (FIG. 3B). In some embodiments, bubble traps 35 are small pockets of space having a volume of between about 50 μL and 500 μL and capable of supporting a pressure of up to 2 bar. Bubble traps 35 can be positioned in series with a microchannel 33 or adjacent to a microchannel 33 or a test chamber 34. Bubble traps 35 are configured to be filled by a flow of fluid, whereupon any air bubbles that occur in the flow of fluid become trapped upon arriving within a bubble trap 35. In some embodiments, bubble traps 35 can be fluidly connected to a degassing valve. In some embodiments, the degassing valve is closed in the presence of a liquid and open in the presence of a gas to release gas pockets and bubbles. In some embodiments, the degassing valve can be manually opened and closed to release air bubbles that are captured in bubble traps 35. Microchannel layer 30 further comprises at least one vacuum port 36 fluidly connected to a vacuum channel 37 that extends towards test chamber 34 but is fluidly isolated from test chamber 34. In certain embodiments, microchannel layer 30 further comprises one or more alignment slots 38. The one or more alignment slots 38 are embedded in the top surface of microchannel layer 30 and are able to accept a guide rod or guide wire (not pictured) to guide the alignment of microchannel layer 30 with the one or more alignment slots of successive layers.

Figure 4:
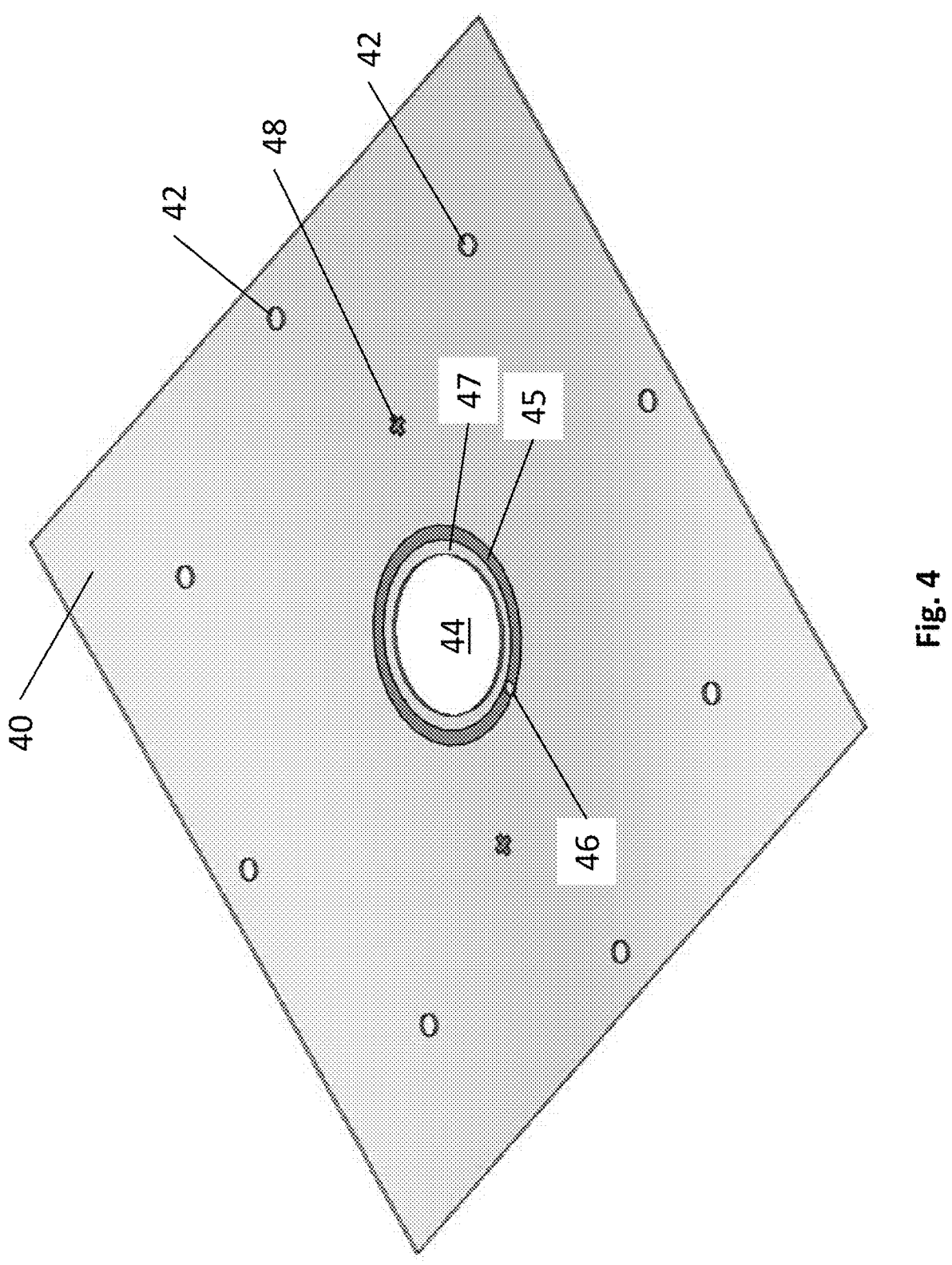
FIG. 4 depicts the cover layer of an exemplary microfluidic device.

Referring now to FIG. 4, an exemplary cover layer 40 is depicted. Cover layer 40 has a substantially planar shape with a top surface, a bottom surface, and a thickness in-between. Cover layer 40 can have any suitable dimensions, such as a length and a width between about 5 and 15 cm, and a thickness between about 0.1 and 1 mm. Cover layer 40 comprises a plurality of well openings 42 arranged around a centrally positioned test chamber opening 44. Well openings 42 and test chamber opening 44 extend through the thickness of cover layer 40 between its top surface and bottom surface. Indent 45 is embedded within the top surface of cover layer 40 and borders test chamber opening 44 with a space in-between to form lip 47. Indent 45 further comprises at least one aperture 46 that extends through to the bottom surface of cover layer 40. Well openings 42, test chamber opening 44, and indent 45 can have any suitable dimensions. In various embodiments, well openings 42 can have a diameter of between about 0.5 and 2.5 mm, test chamber opening 44 can have a diameter of between about 5 and 25 mm, and indent 45 can have a depth of between about 0.1 and 1 mm and can be spaced apart from test chamber opening 44 by a distance between about 0.5 and 2.5 mm. In certain embodiments, the dimensions and layout of cover layer 40 mirrors the dimensions and layout of microchannel layer 30, such that cover layer 40 and microchannel layer 30 have the same length and width, wells 32 and well openings 42 have the same dimensions and positioning, and test chamber 34 and test chamber opening 44 have the same dimensions and positioning. In certain embodiments, cover layer 40 further comprises one or more alignment slots 48. The one or more alignment slots 48 extend through cover layer 40 from its top surface to its bottom surface and are able to accept a guide rod or guide wire (not pictured) to guide the alignment of cover layer 40 with microchannel layer 30.

Figure 5:
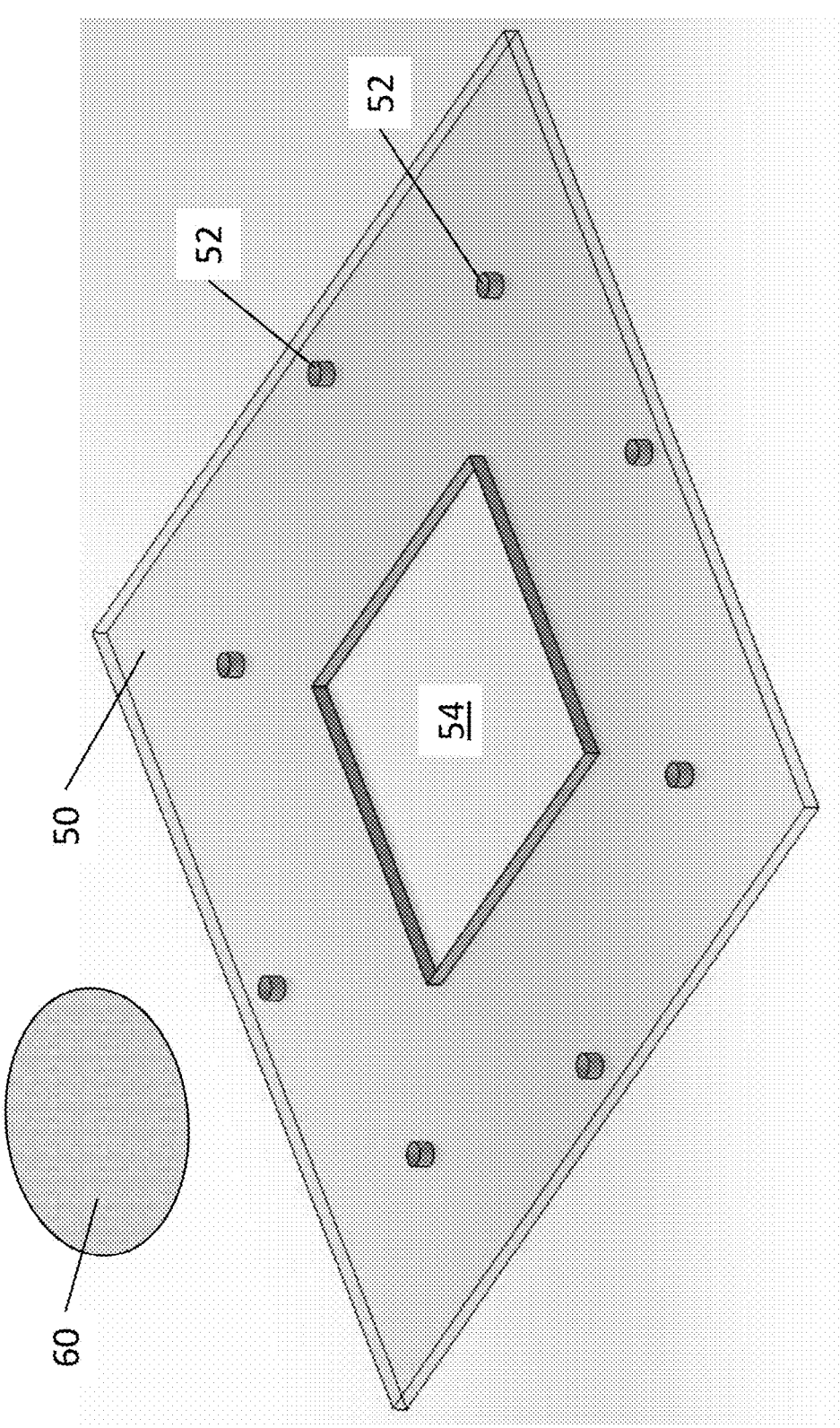
FIG. 5 depicts the upper support layer and coverslip of an exemplary microfluidic device.

Referring now to FIG. 5, an exemplary upper support layer 50 is depicted. Upper support layer 50 has a substantially planar shape with a top surface, a bottom surface, and a thickness in-between. Upper support layer 50 can have any suitable dimensions, such as a length and a width between about 5 and 15 cm, and a thickness between about 0.5 and 5 mm. Upper support layer 50 comprises a plurality of well openings 52 arranged around a centrally positioned window 54. Well openings 52 and window 54 extend through the thickness of upper support layer 50 between its top surface and bottom surface. Well openings 52 and window 54 can have any suitable dimensions. In various embodiments, well openings 52 can have a diameter of between about 0.5 and 2.5 mm, and window 54 can have a length and a width between about 5 and 35 mm. In certain embodiments, the dimensions and layout of upper support layer 50 mirrors the dimensions and layout of microchannel layer 30 and cover layer 40, such that upper support layer 50, microchannel layer 30, and cover layer 40 have the same length and width, well openings 52, well openings 42, and wells 32 have the same dimensions and positioning, and window 54 provides access to test chamber opening 44 and test chamber 34. In certain embodiments, upper support layer 50 further comprises one or more alignment slots (not pictured). The one or more alignment slots may extend through upper support layer 50 from its top surface to its bottom surface and are able to accept a guide rod or guide wire to guide the alignment of upper support layer 50 with microchannel layer 30 and cover layer 40.

Further depicted in FIG. 5 is an exemplary coverslip 60. Coverslip 60 has a substantially planar shape and may be constructed from a rigid material. Coverslip 60 can have any suitable dimensions, such as a length and a width between about 5 and 35 mm. In some embodiments, coverslip 60 is sized to fit within window 54 of upper support layer 50. In some embodiments, coverslip 60 is sized to cover test chamber opening 44, lip 47, and indent 45.

Microchannel layer 30, cover layer 40, upper support layer 50, and coverslip 60 are stacked together to form the microfluidic device 10 depicted in FIG. 1. Cover layer 40 placed on the top surface of microchannel layer 30 seals the plurality of microchannels 33, vacuum port 36, and at least a portion of vacuum channel 37, and maintains the opening to the plurality of wells 32, test chamber 34, and the portion of vacuum channel 37 adjacent to aperture 46. Upper support layer 50 placed on the top surface of cover layer 40 maintains the opening to the plurality of well openings 42 and wells 32 as well as test chamber opening 44 and test chamber 34. Coverslip 60 placed within window 54 of upper support layer 50 and on top of cover layer 40 forms a seal over test chamber opening 44 and indent 45. As described elsewhere herein, lower support layer 20 may be attached to the bottom surface of microchannel layer 30 to enhance its structural rigidity.

An assembled microfluidic device 10 forms two fluidly isolated microfluidic circuits. The first microfluidic circuit comprises the fluid connection between vacuum port 36, vacuum channel 37, aperture 46, and indent 45. Vacuum port 36, connectable to an external vacuum source, can apply a negative pressure in indent 45 by way of vacuum channel 37 and aperture 46 to hold a coverslip 60 on top of cover layer 40. A vacuum source can apply a negative pressure, between about 0.3 and 0.9 atm, to hold coverslip 60 in place and close the opening to test chamber 34. The second microfluidic circuit comprises the fluid connection between each well 32, the microchannel 33 connected to each well 32, and test chamber 34 having a coverslip 60 in place. One or more flowable substances may enter a first well 32 by way of a first well opening 52 and a first well opening 42, flow through a connected first microchannel 33 to enter test chamber 34, exit through a second connected microchannel 33, and flow out of a second well 32.

As the one or more flowable substances pass through test chamber 34, the one or more fluid streams may diffuse into each other to form a gradient of flowable substances. In some embodiments, the gradient of flowable substances can tuned, such as by adjusting the flow rate of each of the flowable substances, by providing a microfluidic device 10 having differing patterns of well openings 52 and microchannels 33, by providing a textured or patterned test chamber 34, and the like. The gradient can be monitored using bright field visualization, fluorescent microscopy, dyes, and the like.

Figures 6A, 6B:
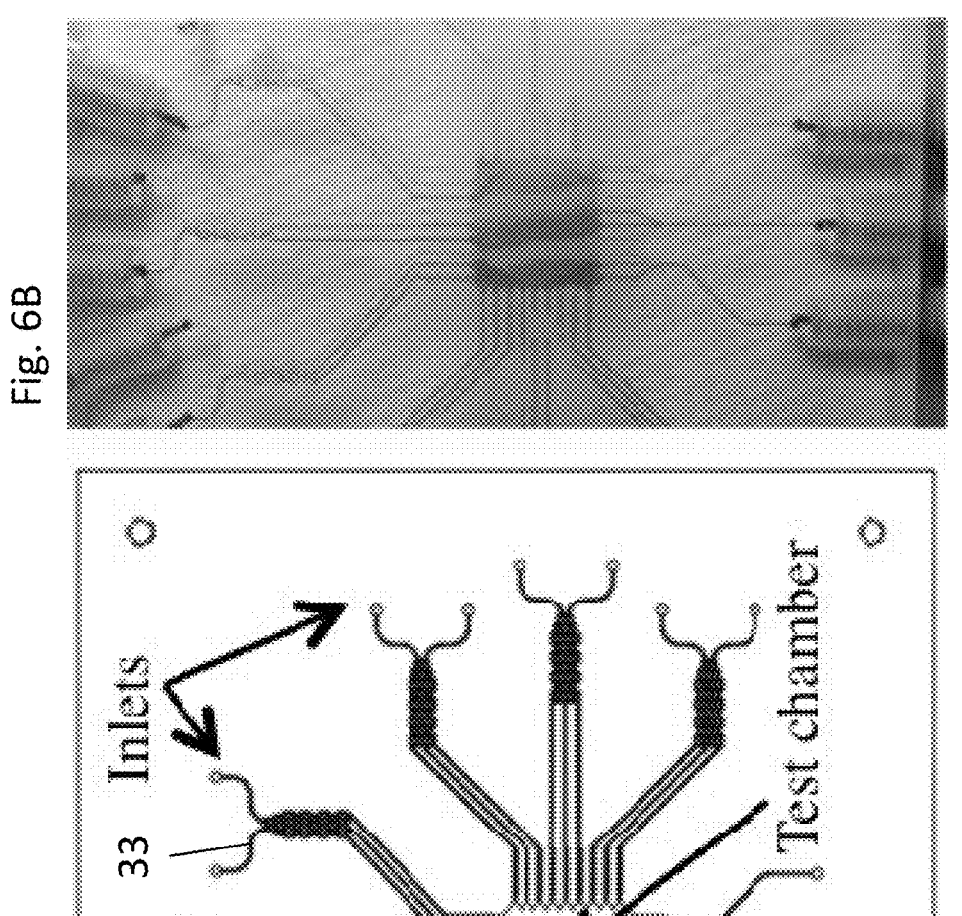
FIG. 6A and FIG. 6B depicts the layout of an exemplary microfluidic device.
Figure 7:
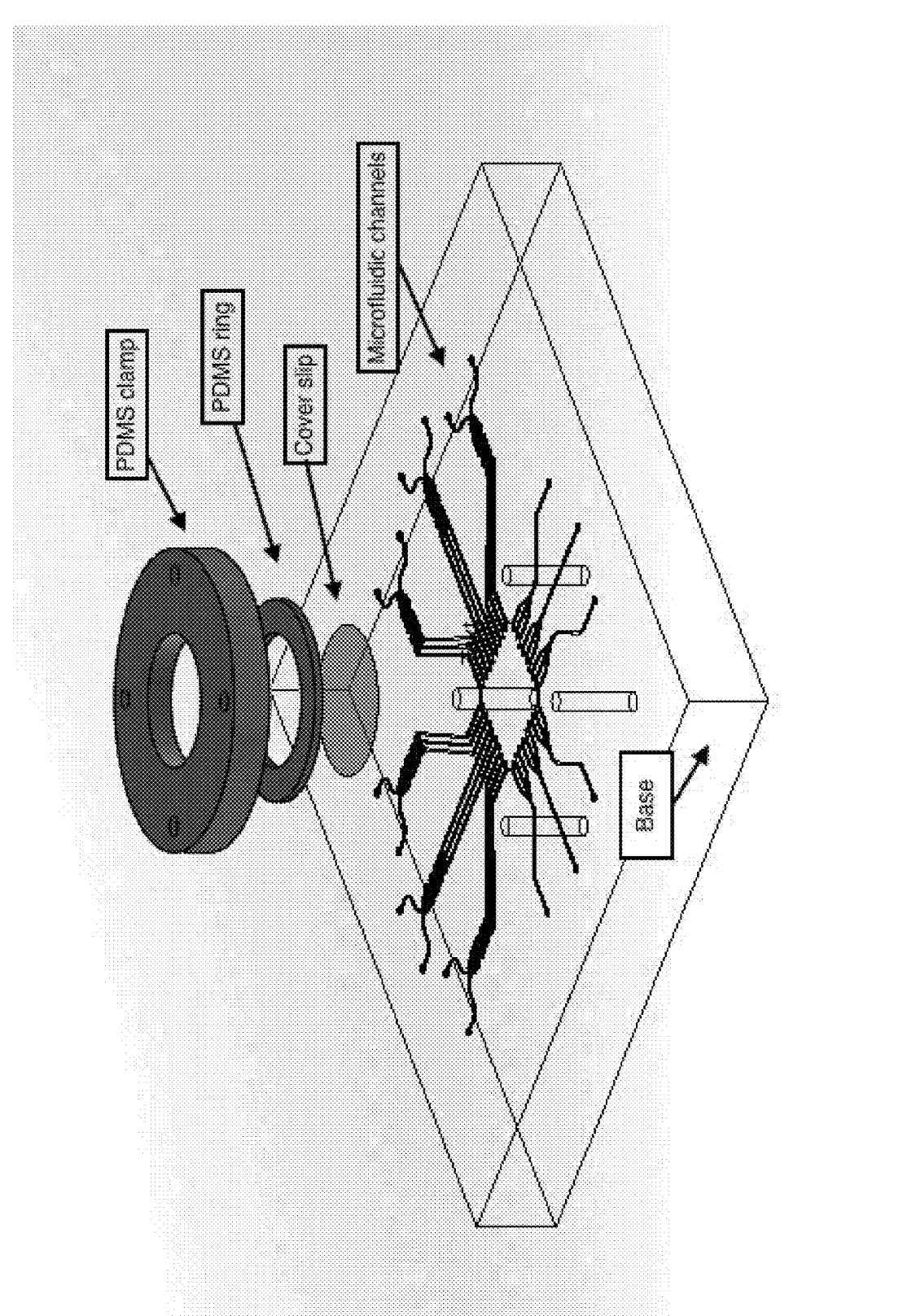
FIG. 7 depicts an exemplary microfluidic device having a clamp system to secure a coverslip.

It should be understood that the components of the microfluidic device are not limited to the specific examples described herein. The various features of the components of the microfluidic device are amenable to any suitable configuration and variation. For example, in FIG. 6A and FIG. 6B, two or more microchannels 33 may combine together or split off into two or more microchannels 33. In certain embodiments, a diffusor region 70 comprises two or more microchannels 33 interconnecting multiple times, such that the fluids of the two or more microchannels 33 may diffuse into each other to form a gradient of fluids that may continue to flow through two or more microchannels 33 downstream from the diffusor region 70. In another example, coverslip 60 may be secured in place by an external clamp, as depicted in FIG. 7. The flow of fluids may also be driven by positive pressure, negative pressure, or by capillary action.

The components of the microfluidic device of the present invention can be made using any suitable method known in the art. The method of making may vary depending on the materials used. For example, components substantially comprising a metal may be milled from a larger block of metal or may be cast from molten metal. Likewise, components substantially comprising a plastic or polymer may be milled from a larger block, cast, or injection molded. Suitable methods can also include the incorporation of one or more elements including circuitry, electrodes, magnets, diodes, and the like. The one or more elements may add one or more functions to the device, such as providing a magnetic field, an electric field (such as in electroporation), a heat source, a cooling source, a light source, and the like.

In some embodiments, the components may be made using 3D printing or other additive manufacturing techniques commonly used in the art, including but not limited to fused deposition, stereolithography, sintering, digital light processing, selective laser melting, electron beam melting, and laminated object manufacturing. The components may be individually printed or at least partially printed together to minimize assembly. Any number of materials compatible with additive manufacturing can be used, such as various polymers, including silicone and ABS; metals, including aluminum, stainless steel, and titanium; and other materials, including ceramics and composites.

In certain embodiments, the components of the microfluidic device can be transparent or translucent. The microfluidic device can be entirely transparent or can include components that are entirely transparent or only transparent in certain parts. For example, portions of microchannel layer 30, cover layer 40, upper support layer 50, and coverslip 60 may be transparent to enable visualization of one or more fluids passing through the microchannels 33. Transparent portions of the microfluidic device can also support certain light-based techniques, such as photoporation, luminescence assays, and optical scanning.

In certain embodiments, the components of the microfluidic device of the present invention can be modified with one or more layers, coatings, and surface treatments. The layers, coatings, and surface treatments may enhance the attachment of molecules or cells, or may enhance the flow of fluids by altering the hydrophobicity or hydrophilicity of certain surfaces. The layers, coatings, and surface treatments described above can be deposited or applied using any suitable means, including spin coating, dip coating, chemical vapor deposition, chemical solution deposition, physical vapor deposition, liquid bath immersion, and the like. The layers, coatings, and surface treatments can be deposited or applied with any suitable thickness.

In various embodiments, the one or more surface treatments can include one or more extracellular matrix material and/or blends of naturally occurring extracellular matrix material to enhance the attachment and viability of live cells, including but not limited to collagen, fibrin, fibrinogen, thrombin, elastin, laminin, fibronectin, vitronectin, hyaluronic acid, chondroitin 4-sulfate, chondroitin 6-sulfate, dermatan sulfate, heparin sulfate, vixapatin (VP12), heparin, and keratan sulfate, proteoglycans, and combinations thereof. Some collagens that may be beneficial include but are not limited to collagen types I, II, III, IV, V, VI, VII, VIII, IX, X, XI, XII, XIII, XIV, XV, XVI, XVII, XVIII, and XIX. These proteins may be in any form, including but not limited to native and denatured forms. In various embodiments, the one or more surface treatments can include one or more carbohydrates such as chitin, chitosan, alginic acids, and alginates such as calcium alginate and sodium alginate. These materials may be isolated from plant products, humans or other organisms or cells or synthetically manufactured.

Methods of Using the Microfluidic Device

The present invention also relates to methods of using the microfluidic device. Referring now to FIG. 8, an exemplary method 100 of using a microfluidic device of the present invention is depicted. Method 100 begins with step 102, wherein a microfluidic device comprising a substrate having a test chamber opening fluidly connected to at least one inlet well opening and at least one outlet well opening by at least one embedded microchannel is provided. In step 104, the test chamber opening is closed with a coverslip. In step 106, at least one fluid source is attached to each of the at least one inlet well opening. In step 108, at least one vacuum source is attached to each of the at least one outlet well opening. In step 110, a negative pressure is applied using the at least one vacuum source, drawing fluid from each of the at least one inlet well opening, through the closed test chamber, and out of the at least one outlet well opening.

Method 100 can be useful in high throughput flowing of at least one fluid at a range of concentrations over a test sample within the test chamber 34. Simultaneous flow of a plurality of fluids over a test sample causes each of the plurality of fluids to diffuse into each other within the test chamber 34, such that the test sample placed within the test chamber 34 is exposed to a gradient of fluids. In certain embodiments, the test sample is placed on the bottom surface of test chamber 34. In other embodiments, the test sample is immobilized on coverslip 60 and inverted into test chamber 34, such that the coverslip 60, when sealing test chamber 34, also suspends the test sample within test chamber 34. The test sample can be immobilized by culturing on coverslip 60, by use of an adhesive, or by use of a sample holder, such as a slice mesh.

In one aspect the present invention provides methods of delivering one or more agents of interest to a population of cells. For example, in certain embodiments, the microfluidic device described herein is used to deliver a gradient of one or more agents to a population of cells within the test chamber of the device. Exemplary agents include, but is not limited to, nucleic acid molecules, DNA, RNA, peptides, proteins, small molecules, dyes, hormones, vitamins, growth factors, stem cell factors, and the like.

In certain embodiments, each well of the device comprises a fluid comprising one or more agents to be delivered via the microchannels to the test chamber. In certain embodiments, flow from each well is controlled such that a gradient of each agent is produced in the test chamber. Each cell is thereby exposed to a specific amount of each agent, as defined by the cell's position in the test chamber. In certain embodiments, the gradient allows for each cell to be exposed to a unique amount of each agent, thus creating a method in which each cell receives a variable amount of the agent. The present device thereby allows for a high throughput method to evaluate the effect of cellular exposure to a variable level of the agent.

In certain embodiments, the method comprises placing a solution comprising one or more agents in one or more wells of the device, where each of the one or more agents is present at a desired initial concentration. In certain embodiments, each of the plurality of wells comprises a different agent. In certain embodiments, each of the plurality of wells comprise the same agent. In certain embodiments, a first set of the plurality of wells comprise a first agent, while a second set of the plurality of wells comprise a second agent. The present method thereby allows any combination of agents to be delivered from any of the combination of wells. In certain embodiments, a well comprises a plurality of different agents, either at the same or different initial concentrations. In certain embodiments, the method comprises administering a gradient of a first set of one or more agents, replacing the solutions with a second set of one or more agents, and administering a gradient of the second set of one or more agents.

In certain embodiments, the population of cells are continuously or periodically exposed to the one or more agents. For example, in certain embodiments, the device is configured for continuous flow from the wells for several seconds, minutes, hours or days. In one embodiment, the device is configured for periodic flow, where flow from the wells is initiated and stopped such that the cells are periodically exposed to the one or more agents. For example, in certain embodiments, the device is configured for exposure to the agents for a defined duration. In one embodiment, the method comprises delivering the agents to the cells for at least one minute, at least 2 minutes, at least 3 minutes, at least 4 minutes, at least 5 minutes, at least 10 minutes, or at least 30 minutes per hour. In one embodiment, the method comprises delivering the agents to the cells for at least one minute, at least 2 minutes, at least 3 minutes, at least 4 minutes, at least 5 minutes, at least 10 minutes, at least 30 minutes, at least 1 hour, at least 2 hours, at least 4 hours, at least 6 hours, at least 12 hours, or at least 18 hours per day.

In certain embodiments, the method comprises evaluating the effect of the delivered agents. For example, the cells may be evaluated using any known methodology or assay known in the art. In one embodiment, the method comprises visual inspection of one or more cells of the test chamber using microscopy, including, but not limited to, fluorescent microscopy, confocal microscopy, near-IR microscopy, two-photon microscopy, and the like. In certain embodiments, the method comprises performing immunocytochemistry, immunohistochemistry, or in situ hybridization to evaluate the presence or abundance of a biomolecule (e.g., protein, antigen, nucleic acid sequence) of interest in the cells of the test chamber. In certain embodiments, the method comprises evaluating the viability or cytotoxicity of the cells of the test chamber. In certain embodiments, the method comprises performing a functional cell-based assay to evaluate the physiology or pathophysiology of the cells of the test chamber.

In certain embodiments, the method comprises determining the concentration or amount of agent which one or more identified cells were exposed to during administration of the gradient. For example, in certain embodiments, the position within the chamber of one or more cells which display an observed characteristic can be used to determine how much of each agent the cell was exposed to. Agent concentration can be calculated using a calibration curve and image analysis of the test chamber during flow, wherein the pixel intensity of the image is correlated to agent concentration. Agent concentration can also be calculated using computer simulations or by solving the advection-diffusion equation with appropriate boundary conditions. Thus, the method allows for the precise correlation of the amount of agent to an observed cellular characteristic.

The population of cells cultured within the test chamber may be of any suitable type of cell, including, but not limited to, eukaryotic, prokaryotic, or mammalian cells. In certain embodiments, the cells are stem cells including, but not limited to, embryonic stem cells (ESCs), pluripotent stem cells (PSCs), induced pluripotent stem cells (iPSCs), adult stem cells, or mesenchymal stem cells (MSCs). In certain embodiments, the cells are from a mammal, including but not limited to human, non-human primate, mouse, rabbit, rat, goat, guinea pig, horse, and the like. A non-mammalian eukaryotic cell includes a yeast cell, a plant cell, an insect cell, a protozoan cell and a fungal cell, including filamentous and non-filamentous fungi. When the cell is a prokaryotic cell, the cell is a bacterial cell. The cells may comprise a differentiated cell and/or a non-dividing cell. The cells may also comprise a progenitor cell or a stem cell. In certain embodiments, the cells comprise is a tissue-specific cell, for example a mammalian tissue-specific cell or a human tissue-specific cell. Exemplary mammalian cells include, but are not limited to epithelial cells, astrocytes, neurons, fibroblasts, cardiomyocytes, embryonic fibroblasts, keratinocytes, adult stem cells, embryonic stem cells, and hepatocytes. In certain embodiments, the cells are phenotypically-pliable cells. Phenotypically-pliable cells are cells whose phenotype is amenable to changing under the conditions of the method of the invention. Non-limiting examples of phenotypically-pliable cells include neurons, fibroblasts, embryonic fibroblasts, adult stem cells and embryonic stem cells.

In certain embodiments, the cells comprise a dispersed cell culture. In certain embodiments, the cells are in the form of a 3D tissue section, including, for example a brain slice. In certain embodiments, the cells are of a primary cell culture or slice culture.

The method of the invention may be carried on a cell comprising a cellular process. Such a cellular process includes, but is not limited to, an electrical property such as an action potential, a dendrite, an axon, a microvilli, a cilia, a stereocilia, a process, an astrocytic process, and the like. As demonstrated herein, this method advantageously permits the introduction of a desired amount of nucleic acid into one or more local sites, permitting the controlled and localized production of protein in physiological amounts, resulting in a multigenic effect in a cell. This method thus allows specific localization of exogenously applied agent (e.g., nucleic acid) without resorting to severing the cellular process from the cell to which it is attached (Kacharmina, et al., 2000, Proc. Nat'l Acad. Sci. USA, 97:11545-11550).

The present invention provides methods of introducing one or more agents into a cell to produce a phenotype-conversion in the cell. For example, in certain embodiments, the method comprises using the methods and microfluidic device described herein to introduce a gradient of the one or more agents to a population of cells in the test chamber. In certain embodiments, the method comprises identifying the identity and amount of the one or more agents that causes a change in phenotype of one or more cells of the test chamber. The difference in phenotype may be any difference, such a difference in species, tissue type, extent of differentiation, exposure to a drug or pathogen, disease state, growth conditions and so forth, wherein the difference is known or suspected of resulting from a difference in gene expression.

In certain embodiments, the one or more agents comprise a nucleic acid molecule, including but not limited to DNA, ssDNA, cDNA, RNA, mRNA, ncRNA, microRNA, hnRNA, total RNA, non-coding RNA, siRNA, shRNA, antisense RNA, and the like.

The one or more nucleic acid molecules may comprise two or more nucleic acids having different sequences. In some embodiments, the two or more nucleic acids encode different polypeptides. In other embodiments, the nucleic acids are non-coding RNAs or other non-coding nucleic acids. In yet other embodiments, the nucleic acids comprise a mixture of coding and non-coding nucleic acids. Nucleic acids may be obtained from a donor cell or may be chemically synthesized or a combination thereof. Methods for chemically synthesizing a nucleic acid are disclosed elsewhere herein and can include in vitro transcription.

In certain embodiments, the one or more agents comprise one or more agents of a donor cell. For example, in one embodiment, the method comprises identifying which and how much of the one or more agents of the donor cell causes the one or more cells of the test chamber to exhibit a change in phenotype to exhibit one or more phenotypic characteristics of the donor cell. The phenotype of the donor cell is different from the phenotype of the cells of the test chamber.

In certain embodiments, the one or more agents comprise one or more mRNA of an mRNA transcriptome of a donor cell. In certain embodiments, the one or more agents comprise the mRNA transcriptome. An mRNA transcriptome may comprise mRNAs encoding 3 or more, 5 or more, 10 or more, 20 or more, 40 or more, 50 or more, 75 or more, 100 or more, 200 or more different polypeptides. For example, in certain embodiments, one or more mRNA of the mRNA transcriptome can be placed in different wells of the device.

Nucleic acid molecules suitable for use in the method of the invention may be of any size. The present invention comprises transfecting a nucleic acid molecule of about 30 bases, about 50 bases, about 75 bases, about 100 bases, about 150 bases, about 200 bases, about 300 bases, about 500 bases, about 750 bases, about 1000 bases, about 1500 bases, about 2000 bases, about 2500 bases, or about 3000 bases, in length. In certain embodiments, the present invention comprises transfecting, sometimes by phototransfection, a mixture of RNAs encoding different proteins and of different molecular weights. In some embodiments, the nucleic acid is an mRNA transcriptome having a range of mRNA transcript sizes and having an average mRNA transcript size from about 0.5 kb to about 5 kb, or in some embodiments, from about 1 kb to about 3.5 kb.

In the method of the invention, nucleic acid is transferred into a cell to initiate phenotype conversion in the recipient cell. As used herein, phenotype conversion comprises a change in at least one of gene expression, protein expression, immunological markers, morphology, physiology, synthesis of bioproducts (e.g., dopamine) and membrane lipid composition. In one embodiment, the change yields a phenotype associated with or indicative of the cell from which the transfected RNA or DNA is obtained. In one embodiment, phenotype conversion in the cell comprises two or more changes. In some embodiments, phenotype conversion comprises three or more changes. In one embodiment, phenotype conversion comprises a change in physiology. In another embodiment, phenotype conversion comprises a change in morphology and a change in physiology of the recipient cell. Phenotype conversion may be accompanied by changes in expression in hundreds of genes. For instance, expression of genes quiescent in both the donor and the recipient cells may be de novo up-regulated. Genes associated with chromosomal remodeling, such as genes involved in chromosome and DNA metabolism related process, may be up-regulated in cells having phenotype conversion. Genes annotated "BP" in the Gene Ontology ("GO") database are considered associated with chromosomal remodeling (The Gene Ontology Consortium (2000) "Gene ontology: tool for the unification of biology," Nature Genet. 25:25-29). The GO database is publicly available (see www-.geneontology.org). In some embodiments, at least about 5%, in some embodiments about 7%, 10%, 15% and in some embodiments at least about 25% of genes that are expressed differently in the recipient cell compared to the donor cell (e.g., differentially expressed genes) based on gene expression profiling have their expression changed to the level observed for the donor cell.

Phenotype conversion in the cell is maintained stably for extended periods of time. In one embodiment, phenotype conversion is stable and persists for at least about 1 day, 2 days, 3 days, 4 days, 5 days, 6 days, 7 days, 8 days, 9 days, 10 days, 11 days, 12 days, 13 days, or more. In one embodiment, phenotype conversion is stable for at least about 1 week, 2 weeks, 3 weeks, 4 weeks, or more. In another embodiment, phenotype conversion is stable for at least about 1 month, 2 month, 3 months or more. In certain embodiments, phenotype conversion is stable for the duration of the cell's lifespan or the lifespan of a culture derived from the cell.

As another non-limiting example, a nucleic acid expression profile of a cell in a desired physiological state (e.g., during differentiation, in a disease state, after treatment with a pharmaceutical, toxin, transcription inhibitor, or other compound) and a nucleic acid expression profile of a cell in another physiological state (e.g., the same cell type pre- or post-differentiation, not in a disease state, or before treatment with a pharmaceutical, toxin, transcription inhibitor or other compound) can be obtained using techniques for RNA isolation known in the art and disclosed elsewhere herein. The cDNA clones of these RNAs can be generated, reflecting the altered RNA abundances of the differing physiological states, or the RNA can be transfected into a cell without first reverse transcribing the RNA to cDNA. These RNA can be mixed according to the same ratios and abundances indicated by the nucleic acid expression profiles of the cells in differing physiological states. These nucleic acid mixtures are then transfected into a cell using the transfection methods disclosed herein, and those known in the art. The methods of the present invention permit the local transfection of a cell, and therefore the nucleic acid mixture can be locally transfected to a specific part of a cell, or the nucleic acid mixture can be generally transfected into a cell by transfecting any portion of the cell. Using the methods of the present invention, and the physiologically relevant mixtures of nucleic acids described herein, once the mixture of nucleic acids is expressed in a cell, the phenotype of the physiological state can be replicated in a cell or a cellular process, thus allowing the skilled artisan to observe the phenotype transfer in a cell or cellular process.

One or more nucleic acid molecules may be obtained from any cell of interest in any physiological state. The donor cell may be any type of cell. A donor cell may be a eukaryotic cell or a prokaryotic cell. In certain embodiments, the eukaryotic cell is a mammalian cell, including but not limited to human, non-human primate, mouse, rabbit, rat, goat, guinea pig, horse cell, and the like. A non-mammalian eukaryotic cell includes a yeast cell, a plant cell, an insect cell, a protozoan cell and a fungal cell, including filamentous and non-filamentous fungi. When the cell is a prokaryotic cell the cell is a bacterial cell. Non-limiting examples of cells from which nucleic acid may be obtained include hepatocytes, astrocytes, cardiomyocytes, neonatal cardiomyocytes, embryonic stem cells, induced pluripotent stem cells, and neurons. RNA from any donor cell of interest can be transfected into any cell in the method of the invention, such as, for example, a fibroblast. In certain embodiments, the donor cells are of the same species as the cells of the test chamber. Donor cells may be from the same individual as the cells of the test chamber, or from a different individual. Donor cells may originate from the same germinal layer (e.g., ectoderm) as the cells of the test chamber (e.g. both arise from ectoderm germ layer), or from a different germinal layer (e.g., one cell arises from ectoderm and the other arises from endoderm germ layer). Donor cells may be the same cell type as the cells of the test chamber but at a different stage of differentiation, exposed to a candidate therapeutic, exposed to a toxin or pathogen, diseased. In yet other embodiments, a donor cell may be a recipient cell. For instance, nucleic acid from a donor cell is transferred into a first recipient cell. Nucleic acid from the first recipient cell is then subsequently transferred into a second recipient cell. In one aspect, the first and second recipient cells are in different physiological states. In another aspect, the first and second recipient cells are the same type of cell. As described elsewhere herein, RNA obtained from a cell may be used to transfect a cell, or may be used as a template to create cDNA. The cDNA may be used in in vitro transcription methods to amplify some or all of the RNA, which is then used in the method of the invention.

As a non-limiting example, the RNA from a donor cell can be isolated from such a cell using techniques known in the art and disclosed elsewhere herein. To obtain an mRNA transcriptome, the total RNA can then be processed using various methods known in the art for isolating mRNA, such as isolation of mRNA using complementary poly-dT nucleic acids, which can be conjugated to beads or a column. One or more mRNA obtained is then transfected into one or more cells using the methods disclosed herein. In certain embodiments, one or more cells of the test chamber then expresses the mixture of mRNA isolated from the donor cell and replicates one or more phenotypic characteristics of the donor cell.

As non-limiting example, the RNA from a cell treated with a compound, such as a drug, a peptide, a cytokine, an antibody, a mitogen, a toxin, a transcription inhibitor or other compounds known in the art, can be isolated using the methods disclosed herein and known in the art. One or more mRNA from that cell can then be transfected into another cell type using the methods disclosed herein, thus transferring the multigenic phenotype of the cell treated with a compound to another cell, thus enabling the rapid and specific determination of that compound on another cell type.

In another non-limiting embodiment of the present invention, the RNA from a diseased cell, such as a tumor cell, a cell harboring an intracellular pathogen, a cell from a patient with an autoimmune disease, and the like, can be isolated from the diseased cell. The mRNA transcriptome from that cell can be isolated from the total RNA using, for example, poly-dT isolation techniques. One or more mRNA from the diseased cell is transfected into another cell using the methods of the present invention, thus transferring the multigenic phenotype of the diseased cell to another cell, providing a more accurate picture of the role interacting nucleic acids and their encoded proteins have in the pheno- type of a cell.

As another non-limiting embodiment of the invention, the method of the invention can be practiced in order to prepare cells for testing therapeutics. Candidate therapeutics are typically tested on a number of different cell types, prior to assessment in animals or humans. These different cells often are cell lines that have a multiplicity of signaling pathways. The multiplicity of pathways may overlap and compensate for drug function and testing with regard to efficacy and/or side effects, thereby making assessment of the candidate drug effects less robust. According, it is contemplated that nucleic acid molecules encoding for one or more specified second messenger system pathways can be transfected into primary cells or cell lines of interest in order to create cells having enriched presence and/or activity of one or more pathways, thus these pathways will dominate over endog- enous pathways. The nucleic acid molecules are therefore a heterogeneous collection that encode the various compo- nents for the one or more second messenger system path- ways. Enriched presence and/or activity of one or more pathways is relative to a cell that has not had nucleic acid molecules encoding one or more specified second messenger system pathways transfected into it. Candidate therapeutics can then be assessed for efficacy and/or side effects on the dominant pathways present in the cells with enriched expression of one or more specified second messenger system pathways. Non-limiting examples of second mes- senger systems include: the cAMP system; the phosphoino- sitol system; the arachidonic acid system; the cGMP system; and the tyrosine kinase system. It is expected that using such defined cell types permits improved assessment of the effect of a candidate on particular pathways. In one embodiment, modulation of endogenous pathways by decreasing expres- sion of particular pathways is also contemplated. Modula- tion can be achieved by introducing siRNAs corresponding to mRNAs encoding particular proteins in a pathway into the cell to inhibit particular pathways. Such modulation can be performed simultaneously with the introduction of the nucleic acid molecules encoding the one or more specified second messenger system pathways, or can be done in one or more separate steps.

When a mixture of nucleic acids, such as a mixture of RNAs is transfected into a cell, subpopulations of that mixture can be transfected into a cell to determine the core set of RNAs responsible for a given phenotype. As a non-limiting example, when the total RNA is isolated from a cell in a certain physiological state and mRNA is isolated from that population of total RNA, specific subpopulations of the isolated mRNA can be transfected into a cell to establish the core mRNAs responsible for that phenotype. The present embodiment can also be performed with cDNA produced from mRNA. Specific populations of mRNA can be identified using sequence homology data or other char- acteristic features known in the art and available from various databases, such as GenBank® (United States Department of Health and Human Services, Bethesda MD).

Alternatively, the mRNA from a cell can be isolated and transfected into a cell using the methods of the present invention, and an siRNA, microRNA, antisense nucleic acid or ribozyme (collectively referred to as an inhibitory nucleic acid) can be transfected along with the mRNA, resulting in silencing and/or inhibition of an mRNA. Silencing an mRNA permits one of skill in the art to identify, for instance, the core mRNA(s) responsible for a multigenic phenotype. In addition, the present invention allows the replication of a phenotype in another cell without the step of determining the nucleic acid expression profile of a cell in a physiological state. The nucleic acid, such as RNA, from a cell in a specific physiological state, such as a certain differential or disease state, can be isolated. In some embodiments, an mRNA transcriptome is then isolated. Using the methods of the present invention, the RNA, or a cDNA of the RNA, can be transfected into a cell in order to analyze the phenotype in the transfected cell once the nucleic acid has been expressed. The nucleic acid can be the total RNA from a cell, or a subpopulation of the RNA, such as the mRNA transcrip- tome.

In certain embodiments, the cells of the test chamber are transfected with the one or more nucleic acids administered by way of the microfluidic device. The cells may be trans- fected using any known methodology in the art, including, but not limited to, electroporation, photoporation, lipid- mediated transfection, and the like. For example, in certain aspects, the test chamber is addressable to a light source for phototransfection or to a current source for electroporation.

In certain embodiments, one or more cells of the test chamber is irradiated with a laser at one or more sites located anywhere on the cell, thereby creating temporary poration holes through which the one or more administered nucleic acids may enter the cell.

Physical methods for introducing a nucleic acid molecule into a cell include calcium phosphate precipitation, lipofec- tion, particle bombardment, microinjection, electroporation, phototransfection and the like. Methods for producing cells comprising vectors and/or exogenous nucleic acids are well- known in the art. See, for example, Sambrook et al., Molecu- lar Cloning: A Laboratory Manual (Cold Spring Harbor Press, NY 2012).

Biological methods for introducing a nucleic acid mol- ecule into a cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a nucleic acid molecule into a cell include colloidal dispersion systems, such as macromolecule complexes, nanocapsules, microspheres, beads, and lipid-based systems including oil-in-water emul- sions, micelles, mixed micelles, and liposomes. An exem- plary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, inter- spersed within the lipid bilayer of a liposome, attached to a liposome via a linking molecule that is associated with both the liposome and the oligonucleotide, entrapped in a lipo- some, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Chol") can be obtained from Calbiochem-Behring; dimyristyl phosphatidylglycerol ("DMPG") and other lipids may be obtained from Avanti Polar Lipids, Inc. (Birmingham, AL.). Stock solutions of lipids in chloroform or chloroform/methanol can be stored at about −200 C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

The present invention may further comprise the sequential transfection of one or more cells of the test chamber. Sequential transfection is used herein to refer to a process in which a cell is transfected at a first time point, and then transfected at a second or subsequent time point. As an example, a cell can be transfected on day 1, the result of which is that one or more nucleic acids are introduced into the cell. These nucleic acids can be expressed by the cellular translation complexes or remain silent, or can be inhibited using an inhibitory nucleic acid as disclosed elsewhere herein. On day 2, the same cell can be transfected again, transfecting one or more of the same or dissimilar nucleic acids to the same cell. The present invention is not limited to transfection separated by a day however. Sequential transfection can occur with minutes, hours, days, weeks or months between a first time point and a second time point, provided the transfection occurs to the same cell. Thus, the sequential transfection methods of the present invention are limited only by the lifespan of the cell. Another non-limiting example of sequential transfections comprises a first transfection on Day 1, a second transfection 48 hours later (Day 3) and a third transfection 7 days after the first transfection. The conditions of sequential transfection may be the same or different. The means of transfection may be changed and/or the number of sites transfected in a transfection step may be different among multiple transfections. For instance, the second and subsequent transfections using transfection may be performed using a reduced laser power compared to the laser power used in the first transfection.

The sequential transfection methods of the present application are useful for, among other things, analyzing temporal gene expression in a cell, analyzing the multigenic effects of a protracted developmental process, and determining the relationship of genotype to phenotype over the course of the viable life span of a cell. Sequential transfection using the same nucleic acids also increases the robustness of expression of the phototransfected nucleic acids.

To assess the effect of expression of the transfected nucleic acids, cells transfected in accordance with the method of the invention can be examined using methods known in the art. Assessments may be made, for example, of phenotypic changes, mRNA expression, protein expression and functional assays. Examples of such analyses include, but are not limited to, cell morphology, presence and absence of immunological markers, RT-PCR, expression profiling, mRNA abundance measurements, immunocytochemistry analysis (ICC) for specific proteins, cell viability, and cell-specific activities, such as cell division-mitosis and electrophysiology.

Optionally, the present method further comprises inhibiting transcription in the transfected cell, thus preventing competition between expression of endogenous and exogenous mRNAs and the proteins encoded thereby. Transcription can be inhibited by addition of exogenous agents, such as an inhibitory nucleic acid or compounds that inhibit transcription, such as 5,6-Dichloro-1-β-D-ribofuranosylbenzimidazole (DRB), a protease, or SP100030 (Huang et al., 2001, Br. J. Pharmacol., 134: 1029-1036). Other agents useful for inhibiting transcription in a recipient cell include, but are not limited to, α-amanitin, trichostatin A (TSA; a histone deacetylase inhibitor), tubulin depolymerizer and actin depolymerizer. In certain embodiments, one or more cells of the test chamber is contacted with one or more transcription inhibition agents prior to transfection. In some embodiments, the cell is contacted between about 30 minutes and about 80 hours, or between about 30 minutes and about 60 hours, or between about 6 hours to about 48 hours, prior to transfection.

The nucleic acids useful in the methods of the present invention may comprise a variety of nucleic acids, including various species of RNA (mRNA, siRNA, miRNA, hnRNA, tRNA, total RNA, combinations thereof and the like) as well as DNA. Methods for isolating RNA from a cell, synthesizing a short polynucleotide, constructing a vector comprising a DNA insert, and other methods of obtaining a nucleic acid to phototransfect into a cell are well known in the art and include, for example, RNA isolation, cDNA synthesis, in vitro transcription, and the like.

The nucleic acid compositions of this invention, whether RNA, cDNA, genomic DNA, or a hybrid of the various combinations, may be isolated from natural sources or may be synthesized in vitro. Techniques for nucleic acid manipulation are described generally in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York), incorporated herein by reference. Nucleic acids suitable for use in the present method also include nucleic acid analogs. Examples of such analogs include, but are not limited to, phosphorothioate, phosphotriester, methyl phosphonate, short chain alkyl or cycloalkyl intersugar linkages, or short chain heteroatomic or heterocyclic intersugar ("backbone") linkages. In addition, nucleic acids having morpholino backbone structures (U.S. Pat. No. 5,034,506)

or polyamide backbone structures (Nielsen et al., 1991, Science 254: 1497) may also be used.

The methods of the present invention can comprise the use of a variety of nucleic acids, including DNA, RNA, a cDNA reverse transcribed from an mRNA, an RNA transcribed from that cDNA, a DNA amplified from the cDNA, an RNA transcribed from the amplified DNA, and the like. The present invention further comprises using single-stranded and double-stranded RNA and DNA molecules. Any coding sequence of interest can be used in the methods of introducing and translating a nucleic acid in a cell or in a cellular process, such as a dendrite. One of skill in the art will understand, when armed with the present disclosure, that a multitude of properties of a cellular process, and by association, of the attached cell, can be affected by the methods of the present invention.

In one embodiment of the present invention, the nucleic acid transfected into a cell is all or a portion of the total mRNA isolated from a biological sample. The term "biological sample," as used herein, refers to a sample obtained from an organism or from components (e.g., organs, tissues or cells) of an organism. The sample may be of any biological tissue or fluid. The nucleic acid (either genomic DNA or mRNA) may be isolated from the sample according to any of a number of methods well known to those of skill in the art.

Methods of isolating total mRNA are well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993)).

In one embodiment, the total nucleic acid is isolated from a given sample using, for example, an acid guanidinium-phenol-chloroform extraction method and polyA$^+$ mRNA is isolated by oligo dT column chromatography or by using (dT)n magnetic beads. Commercially available products, such as TRIZOL and MICRO-FASTTRACK (Invitrogen™, Carlsbad, CA), are useful in extracting nucleic acid from a biological sample.

The mRNA can be locally transfected directly into a cell or a cellular process, or the sample mRNA can be reverse transcribed with a reverse transcriptase and a promoter comprising an oligo dT and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra.; Van Gelder, et al., 1990, Proc. Natl. Acad. Sci. USA, 87: 1663-1667). Moreover, Eberwine et al. (1992, Proc. Natl. Acad. Sci. USA, 89: 3010-3014) provide a protocol using two rounds of amplification via in vitro transcription to achieve greater than 10$^6$ fold amplification of the original starting material.

The present invention further comprises the use of in vitro transcription for transfection into a cell or cellular process. In vitro transcription comprises the production of dsRNA by transcribing a nucleic acid (DNA) segment in both directions. For example, the HiScribe™ RNAi transcription kit (New England Biolabs, Ipswich, MA) provides a vector and a method for producing a dsRNA for a nucleic acid segment that is cloned into the vector at a position flanked on either side by a T7 promoter. Separate templates are generated for T7 transcription of the two complementary strands for the dsRNA. The templates are transcribed in vitro by addition of T7 RNA polymerase and dsRNA is produced. Similar methods using PCR and/or other RNA polymerases (e.g., T3 or SP6 polymerase) can also be used and are known in the art.

The present invention further comprises the use of chemically synthesized nucleic acids for use in transfection. Oligonucleotides for use as probes can be chemically synthesized according to the solid phase phosphoramidite triester method first described by Beaucage, (1981, Tetrahedron Letts., 22:1859-1862) using an automated synthesizer, as described in Needham-VanDevanter, et al. (1984, Nucleic Acids Res., 12:6159-6168). Purification of oligonucleotides is by either native acrylamide gel electrophoresis or by anion-exchange HPLC as described in Pearson (1983, J. Chrom., 255:137-149). The sequence of the synthetic oligonucleotides can be verified using the chemical degradation method of Maxam (1980, in Grossman and Moldave, eds., Methods in Enzymology, Academic Press, New York, 65:499-560).

The present invention can further comprise the use of DNA in a process to locally transfect a cell or a cellular process via transfection. The DNA can be contained in a vector. The invention includes an isolated DNA encoding a protein operably linked to a nucleic acid comprising a promoter/regulatory sequence such that the nucleic acid is capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Expression of a protein in a cell or a cellular process transfected as disclosed herein may be accomplished by generating a plasmid or other type of vector comprising the desired nucleic acid operably linked to a promoter/regulatory sequence which serves to drive expression of the protein, with or without a tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, as well as the Rous sarcoma virus promoter, and the like. Moreover, inducible and tissue specific expression of the nucleic acid encoding a protein can be accomplished by placing the nucleic acid encoding a protein under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Selection of any particular plasmid vector or other DNA vector is not a limiting factor in this invention and a wide plethora of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The nucleic acids encoding a protein can be cloned into various plasmid vectors. However, the present invention should not be construed to be limited to plasmids or to any particular vector. Instead, the present invention should be construed to encompass a wide plethora of vectors which are readily available and/or well-known in the art.

The present invention further comprises locally transfecting an inhibitory nucleic acid, such as an antisense nucleic acid, an siRNA or an miRNA into a cell. An siRNA polynucleotide is an RNA nucleic acid molecule that interferes with RNA activity that is generally considered to occur via a post-transcriptional gene silencing mechanism. An siRNA polynucleotide can comprise a double-stranded RNA (dsRNA) but is not intended to be so limited and may comprise a single-stranded RNA (see, e.g., Martinez et al., 2002, Cell 110:563-74). The siRNA polynucleotide included in the invention may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5' to 3' phosphodiester linkage). Accordingly it will be appreciated that certain exemplary sequences disclosed herein as DNA sequences capable of directing the transcription of the siRNA polynucleotides are also intended to describe the corresponding RNA sequences and their complements, given the well-established principles of complementary nucleotide base-pairing.

An siRNA may be transcribed using as a template a DNA (genomic, cDNA, or synthetic) that contains a promoter for an RNA polymerase promoter. For example, the promoter can be the U6 promoter or the H1 RNA polymerase III promoter. Alternatively, the siRNA may be a synthetically derived RNA molecule. In certain embodiments, the siRNA polynucleotide may have blunt ends. In certain other embodiments, at least one strand of the siRNA polynucleotide has at least one, and in some embodiments two nucleotides that "overhang" (i.e., that do not base pair with a complementary base in the opposing strand) at the 3' end of either strand of the siRNA polynucleotide. In some embodiments, each strand of the siRNA polynucleotide duplex has a two-nucleotide overhang at the 3' end. The two-nucleotide overhang can be a thymidine dinucleotide (TT) but may also comprise other bases, for example, a TC dinucleotide or a TG dinucleotide, or any other dinucleotide. The overhang dinucleotide may also be complementary to the two nucleotides at the 5' end of the sequence of the polynucleotide that is targeted for interference. For a discussion of 3' ends of siRNA polynucleotides see, e.g., WO 01/75164.

In certain embodiments, siRNA polynucleotides comprise double-stranded polynucleotides of about 18-30 nucleotide base pairs. In certain instances, siRNA polynucleotides comprise about 18, about 19, about 20, about 21, about 22, about 23, about 24, about 25, about 26, or about 27 base pairs, and in other embodiments about 19, about 20, about 21, about 22 or about 23 base pairs, or about 27 base pairs. The siRNA polynucleotide useful in the present invention may also comprise a polynucleotide sequence that exhibits variability by differing (e.g., by nucleotide substitution, including transition or transversion) at one, two, three or four nucleotides from a particular sequence. These differences can occur at any of the nucleotide positions of a particular siRNA polynucleotide sequence, depending on the length of the molecule, whether situated in a sense or in an antisense strand of the double-stranded polynucleotide. The nucleotide difference may be found on one strand of a double-stranded polynucleotide, where the complementary nucleotide with which the substitute nucleotide would typically form hydrogen bond base pairing, may not necessarily be correspondingly substituted. In some embodiments, the siRNA polynucleotides are homogeneous with respect to a specific nucleotide sequence.

Polynucleotides that comprise the siRNA polynucleotides may in certain embodiments be derived from a single-stranded polynucleotide that comprises a single-stranded oligonucleotide fragment (e.g., of about 18-30 nucleotides) and its reverse complement, typically separated by a spacer sequence. According to certain such embodiments, cleavage of the spacer provides the single-stranded oligonucleotide fragment and its reverse complement, such that they may anneal to form, optionally with additional processing steps that may result in addition or removal of one, two, three or more nucleotides from the 3' end and/or the 5' end of either or both strands, the double-stranded siRNA polynucleotide of the present invention. In certain embodiments the spacer is of a length that permits the fragment and its reverse complement to anneal and form a double-stranded structure (e.g., like a hairpin polynucleotide) prior to cleavage of the spacer, and optionally, subsequent processing steps that may result in addition or removal of one, two, three, four, or more nucleotides from the 3' end and/or the 5' end of either or both strands. A spacer sequence may therefore be any polynucleotide sequence as provided herein that is situated between two complementary polynucleotide sequence regions which, when annealed into a double-stranded nucleic acid, result in an siRNA polynucleotide.

The present method further comprises methods for introducing a nucleic acid into a cell. The method comprises transfecting a cell in the presence of a nucleic acid molecule where the nucleic acid molecule is in a fluid medium delivered to the cell using the microfluidic device, thereby permitting the transfer of the nucleic acid from one side of the cell membrane to the other side of the cell membrane through the cell membrane. The fluid medium can comprise any medium having the buffering capacity and pH to support the viability of a cell and the stability of a nucleic acid molecule. Contemplated media include, but are not limited to, Basal Media Eagle (BME), BGJb Medium, Brinster's BMOC-3 Medium, CMRL Medium, $CO_2$-Independent Medium, Dulbecco's Modified Eagle Media (D-MEM), F-10 Nutrient Mixtures, F-12 Nutrient Mixtures, Glasgow Minimum Essential Media, Grace's Insect Cell Culture Media, Improved MEM, IPL-41 Insect Media, Iscove's Modified Dulbecco's Media, Leibovitz's L-15 Media, McCoy's 5A Media (modified), MCDB 131 Medium, Media 199, Medium NCTC-109, Minimum Essential Media (MEM), Modified Eagle Medium (MEM), Opti-MEM® I Reduced Serum Media, RPMI Media 1640, Schneider's Drosophila Medium, Waymouth's MB 752/1 Media, Tris, Tris-EDTA (TE) cell culture media, Williams Media E, artificial spinal fluid (aCSF), Ringer's solution and the like. The present invention can further comprise the use of buffered salt solutions, including, but not limited to, Dulbecco's Phosphate-Buffered Saline (D-PBS), Earle's Balanced Salt Solution, Hanks' Balanced Salt Solution, Phosphate-Buffered Saline (PBS), and the like.

The number of nucleic acid molecules that enter the cell is influenced by the initial nucleic acid concentration in the fluid medium, the size of the nucleic acid molecule, the flow rate of the fluid medium, the position of the inlet and outlet, and the position of the cell within the test chamber. With phototransfection, the number of nucleic acid molecules that enter the cell is influenced by the laser intensity, e.g., the length of each laser pulse and the number of laser pulses delivered. Based on the teachings herein, the skilled artisan can readily adjust the parameters of the transfection process to control the approximate number of nucleic molecules that enter the cell.

In one embodiment, a cell is exposed to a fluid medium comprising a nucleic acid molecule at about 1 to about 150 μg/ml, or at about 10 to about 100 μg/ml, or at about 10 to about 50 μg/ml in the bath.

The present invention further comprises the use of other methods for introducing a nucleic acid to a cell or tissue via transfection. Methods included in the present invention include, for example, perfusion, picospritzing, microinjection and the like. Methods for perfusion include, but are not limited to, using a pump to move a fluid medium comprising a nucleic acid molecule to a cell or tissue. The fluid medium used in the perfusion methods of the present invention can included those disclosed elsewhere herein, such as buffered solutions that support and maintain the stability of a nucleic acid and a cell, tissue or animal. In one embodiment of the present invention, the fluid medium can include a medium, such as Basal Media Eagle (BME), BGJb Medium, Brinster's BMOC-3 Medium, CMRL Medium, $CO_2$-Independent Medium, Dulbecco's Modified Eagle Media (D-MEM), F-10 Nutrient Mixtures, F-12 Nutrient Mixtures, Glasgow Minimum Essential Media, Grace's Insect Cell Culture Media, Improved MEM, IPL-41 Insect Media, Iscove's Modified Dulbecco's Media, Leibovitz's L-15 Media, McCoy's 5A Media (modified), MCDB 131 Medium, Media 199, Medium NCTC-109, Minimum Essential Media (MEM), Modified Eagle Medium (MEM), Opti-MEM® I Reduced Serum Media, RPMI Media 1640, Schneider's Drosophila Medium, Waymouth's MB 752/1 Media, Williams Media E, artificial spinal fluid (aCSF), Ringer's solution and the like. The present invention can further comprise the use of buffered salt solutions, including, but not limited to, Dulbecco's Phosphate-Buffered Saline (D-PBS), Earle's Balanced Salt Solution, Hanks' Balanced Salt Solution, Phosphate-Buffered Saline (PBS), and the like.

The present invention further comprises using picospritzing in conjunction with phototransfection to introduce a nucleic acid to a cell, organ or tissue. Picospritzing comprises the use of electrical pulses with a pressure device to deliver a compound, such as a nucleic acid, to a cell, tissue or animal. Method for picospritzing are known in the art and are described in, for example, Herberholz, et al., 2002, J. Neuroscience, 22: 9078-9085). Picospritzing apparatuses are available from, for example, World Precision Instruments (Sarasota, FL).

In another embodiment, transfection of cells with nucleic acids encoding two or more different polypeptides is effected by microinjection.

When phototransfection is employed, the methods comprise irradiating a cell with a laser to phototransfect and locally transfect the cell. When the laser contacts the cell membrane, or cell wall in the case of plant cells, fungal cells, and other cells comprising a cell wall, the plasma membrane or cell wall is perforated, permitting the diffusion of foreign molecule, such as RNA and/or DNA, to enter the cell. The fluidity of mammalian cell membranes facilitates subsequent closure of the perforation. Lasers compatible with the present invention include, but are not limited to, continuous-wave argon-ion lasers operating at 488 nm (Schneckenburger, et al., 2002, J. Biomed. Opt., 7: 410-416; Palumbo et al., 1996, J. Photochem. Photobiol. B-Biol., 36: 41-46), pulsed and frequency upconverted Nd:YAG lasers operating at 355 nm (Shirahata, et al., 2001, J. Invest. Med., 49: 184-190), 532 nm (Soughayer, et al., 2000, Anal. Chem., 72: 1342-1347), and 1064 nm (Mohanty, et al., 2003, Biotechnol. Lett. 25: 895-899), and femtosecond titanium-sapphire lasers (Tirlapur, et al., 2002, Plant J. 31: 365-374; Tirlapur, et al., 2002, Nature 418: 290-291; Zeira, et al., 2003, Mol. Therapy 8: 342-350). In some embodiments, a titanium-sapphire laser at 405 nm (PicoQuant GmbH, Berlin Germany) is used to phototransfect a cell. However, the present invention is not limited to a titanium-sapphire laser, but includes any laser with the capacity of delivering a localized focal volume of about $10^{-19}$ $m^3$.

Control of the incident laser beam is achieved by using various apparatuses to control the focus and power of the laser, as well as to aim the laser. Focusing the laser is achieved by passing the incident laser through a lens, such as a microscope lens, placed between the laser and the cell. The power of the laser in controlled by modulating the voltage and current going to the laser and through the use of neutral density filters or pockels cells. Exposure of the cells to the laser is controlled through a shutter, such as a single lens reflex (SLR) camera shutter and/or with electronically controlled pockels cells.

Aiming the laser is accomplished through a microscope lens and with dielectric and steering mirrors and AOD (acoustic optical deflector) between the laser source and a cell. A microscope useful in the practice of the present invention includes, but is not limited to, a confocal microscope, a multiphoton excitation fluorescence microscope, a light microscope, and the like. The present method further comprises aiming the laser using an optical fiber to transmit the laser to a distant or difficult-to-access area. As a non-limiting example, an optical fiber is used to phototransfect intestinal, neural or cardiothoracic cells in a live animal. Further, the present invention comprises phototransfecting a cell or a population of cells using multiple optical fibers in an animal. Optical fibers are well known in the art and are described in, for example, U.S. Pat. Nos. 3,711,262 6,973, 245.

A laser beam with less than a milliwatt of power for tens of milliseconds is sufficient to porate a cell (Paterson, et al., 2005, Optics Express, 13: 595-600). In some embodiments, the laser has a power density of about 1200 $MWm^2$ and a total power of about 30-55 mW at the back aperture of the lens. Further, in order to provide maximum surface area for transfection, the laser beam should be highly circular (dx=dy) with beam diameter of about 2 mm.

The starting power output of the laser is attenuated through the use of various filters, such as a neutral density (ND) filter to reduce the power to the milliwatt range required for phototransfection with no attendant pathological effects on the target cell. The beam can be expanded through the use of a telescope where f=100 mm, and directed into a microscope, such as a light microscope or an oil-immersion microscope with a ×100 objective (N.A.=1.25).

An SLR shutter between the laser source and the microscope permits control of the exposure time. An exposure time of about 40 ms is sufficient to porate a cell without attendant damage, but this parameter can be altered to increase or decrease exposure time.

Target cells are positioned and focused on by manipulating the stage of the microscope and/or using dielectric and steering mirrors and AOD, so the beam is focused on the cell membrane and not towards the nucleus of the cell. When porating a cellular process, such as a dendrite, the beam is focused directly on the cellular process.

An exemplary phototransfection protocol comprises at least two and can include three sequential phototransfection steps of a cell. In certain embodiments, the first phototransfection step is at about 35 mW using a titanium-sapphire laser and subsequent phototransfections steps are at a lower power, such as 30 mW or less. In one embodiment, each phototransfection step involves laser irradiating the cell at numerous, random sites. The number of sites per step is determined by consideration of the strength of the laser, the diameter of the pores that result in the irradiated site, the average size of the transcripts in the mRNA transcriptome and modeling transport of individual transcripts through the pore using Brownian dynamics. After the first phototransfection step, the cell may be transferred to a growth medium specific for the donor cell.

In some embodiments, the cells are transfected with a nucleic acid comprising a marker that indicates a successful transfection. Such markers are known in the art and include, for example, antibiotic resistance and fluorescent proteins. Successful transfection can be tracked by the addition of a detectable molecule to the nucleic acid solution. Such molecules are well known in the art. In some embodiments, the molecule is non-toxic to the recipient cell. Non-limiting examples include *Lucifer* yellow and carboxyfluorescein diacetate succinimidyl ester. Expression of the locally transfected nucleic acid is analyzed according to the presence and activity of a marker or the phenotype of the cell.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1: High Throughput Transcriptome Induced Phenotype Remodeling (TIPeR)

Cell types can be distinguished based upon their transcriptomes but there is a range in expression of RNAs that help to define cell type. This produces an issue when performing transgene expression within cells since expression of the transgene will be on a different transcriptomic background in each transfected cell. Thus ideally it would be important to systematically alter the individual transfected RNA abundances used in transfecting multiple cells with the experimental RNA pools. Such an experimental scheme would enable the identification of those cells in which the transfected RNAs interact with the host cell transcriptome to produce a quantifiable functional readout. The following study presents a novel high-throughput microfluidic device specifically developed for Transcriptome Induced Phenotype Remodeling (TIPeR) applications. The device enables large numbers of cells, both dispersed and in the live slice, to be efficiently transfected with large numbers of differing amounts of RNAs. In short, this microfluidic device relies on exquisitely controlled flows (at low Reynolds number) and diffusion of chemical species to a target host cell (FIG. 6A). The diffusion of RNAs is both temporally and spatially controlled (FIG. 6B) using a combination of fluid flow and geometry such that multiple cells and RNAs can be simultaneously investigated inside the device. This microfluidic TIPeR device can be fully automated including experimentation and cell incubation; it can also be multiplexed to analyze several chemical species over a range of investigator-defined concentrations. The device has been engineered to be light addressable so phototransfection can be utilized. Electroporation can also be implemented as a transfection mode.

The schematic in FIG. 6A shows the microfluidic device including channels, mixing geometries, and a central test chamber. The microchannels are approximately 200 μm in width and depth and the test chamber is approximately 2 cm square and 200 μm deep. The schematic in FIG. 6A shows 12 inlets and 6 outlets; each successive pair of inlets is connected by a diffusor to mix species into solutions of user-determined concentrations. These solutions ultimately feed into the test chamber that will contain cells for testing with TIPeR. The center reservoir or test chamber is configured to reversibly interface with standard coverslips or slice mesh for ease of use and is compatible with standard laboratory microscopes.

Air bubbles trapped inside the microchannels and test chambers can alter the function of the microfluidic device. These bubbles can form on the walls of an inlet syringe or well from dissolved gases inside fluids and can enter the microfluidic device during flow and become trapped inside the microchannels and test chambers. This may result in operational failure as the time of experiments increases. The air bubbles can also affect experimental results by altering flow patterns and mixing of fluids and may damage cells by inducing shear stress on cell membranes. To overcome this problem, degassing valves or bubble traps can be integrated into the microchannels and the test chambers to filter out air bubbles. The valves or traps were observed to improve device reliability in experiments that ran fluid through the microfluidic devices for over five hours. Bubble traps can have a very low internal volume (for example, between about 50 μL and 500 μL or about 115 μL) and operate at a wide range of fluid pressures (for example, up to about 2 bar). A low internal volume prevents the need of providing a high quantity of inlet fluid to initially fill the bubble trap.

The design of the embodiment presented in the Figures is capable of simultaneously testing up to twelve different species of RNA on a coverslip or in slice mesh. The test chamber allows for thousands of cells to be exposed to various species and concentrations. Upon transfection of the 12 RNAs across the cells in the concentrations dictated by RNA concentration and flow rates through the chamber, these 12 RNAs can be replaced with 12 different RNAs whose concentrations can also be manipulated though the device followed by phototransfection into the cells. When laser energy and pulse pattern are appropriately selected, multiple phototransfections can be performed on individual cells with no apparent ill effects.

Figures 9A, 9B, 9C:
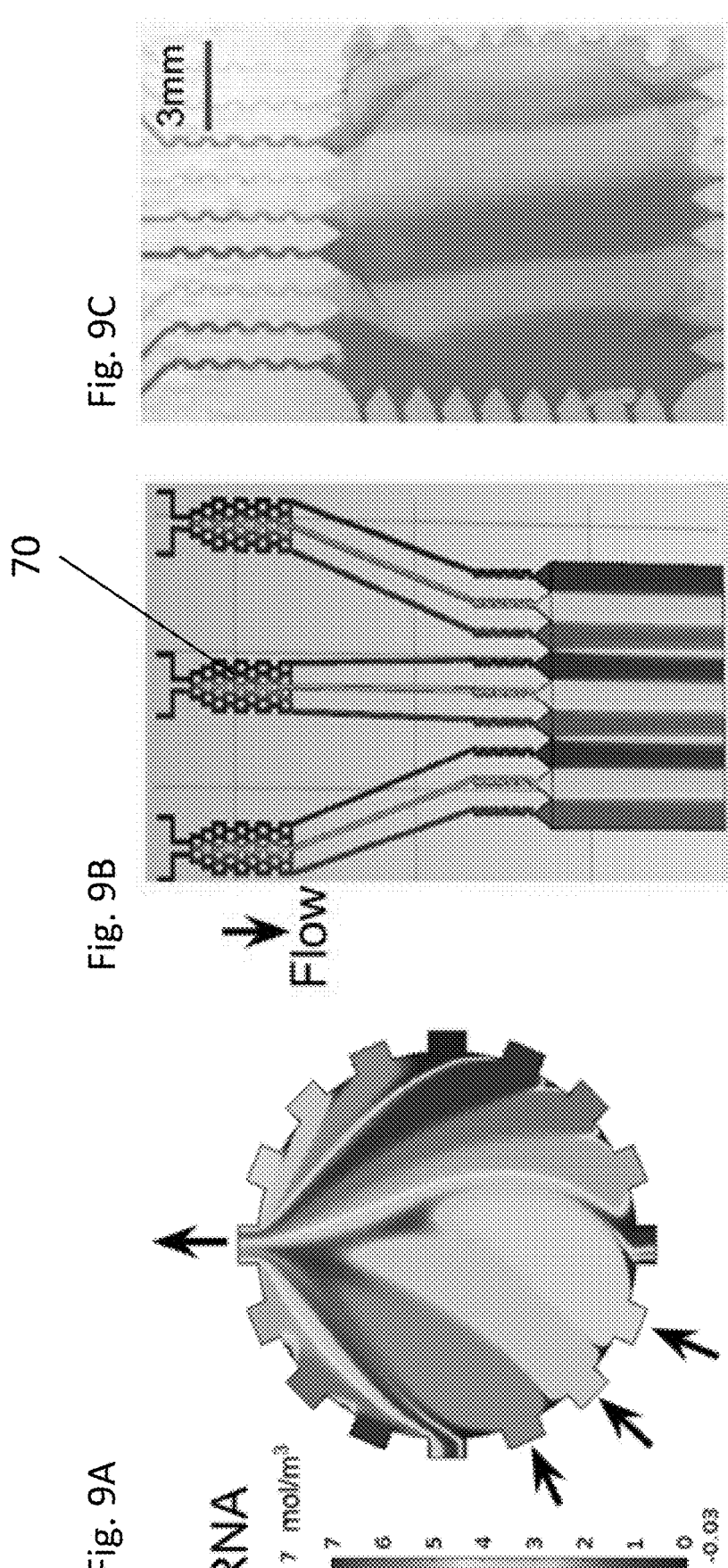
FIG. 9A through FIG. 9C depict the results of testing fluid concentration profiles using the microfluidic device of the present invention.

In addition to the experiments shown in FIG. 9A through FIG. 9C, computational fluid dynamic (CFD) simulations have been performed in order to determine the spatial distribution of RNA in the test chamber so that RNA concentration for all 12 RNAs at any position in the chamber can be determined. In this way, the cell chemical environment can be predicted in detail. FIG. 6B and FIG. 9C show an initial prototype based on the schematic as well as the diffusion and mixing patterns of two different fluids (red and green dyes). The time scale of the experiment is set by the diffusion rate of the chemical species, which is controlled by flow rate and system size. The red and green striations of dye shown in FIG. 6B and FIG. 9C demonstrate the ability to control the flow and mixing of different chemical species, which allow for the rapid multiplexing of RNA at different concentrations.

The initial microfluidic prototype was fabricated using traditional manufacturing techniques. A computerized numerical controlled (CNC) machine with high precision (~1 μm) can robustly produce complex features with dimensions of approximately 100 μm to fabricate the microfluidic device. Multi-axis machining techniques have been used to construct built-in side ports with compression fittings that prohibit leaking, providing extremely reliable fluid injection. Additional micro-features may be added, including nested mixers and diffusers for expanded multiplexing as well as truly three-dimensional (3D) microfluidic devices. Layers of soft materials (e.g. PDMS) have been introduced into the construction of the device that are also gas-permeable, allowing the device to serve as an incubator for monitoring cells after the transfection process. FIG. 9A shows a numerical simulation using computational fluid dynamics techniques in which the concept of obtaining spatially and temporally controlled RNA concentrations was tested in a given test geometry without mixing for RNA application and removal fluidic dynamics. By turning the ports on and off in a sequential manner, concentration patterns are generated with complex topological features. Results clearly show that one can control the concentration magnitude and length-scale (size) of a given chemical species as well as gradients in a given geometry. Next, the experimental geometry is introduced and the flow, mixing, and diffusion of a given chemical species is simulated with mixing (FIG. 9B). The numerical simulations show the full evolution of the concentration profile along the device prototype. As the inlet streams meet in the gridded diffusor, mixing occurs and split into distinct levels before entering the gradient chamber downstream. The three bands of high, intermediate, and low concentrations in the mixing chamber represent the desired level of RNA for transfection exposures.

Next, the numerical simulation results were compared to an experiment under similar conditions (FIG. 9C). The numerical prediction seems to capture the main features of the microfluidic experiments shown in FIG. 9C. Experiments were performed by injecting two dyes (which represent RNA species) at the inlets and observing how they flow, mix, and diffuse into the test chamber. Results show the desired concentrations bands necessary for the multiplexing; in other words, the device is capable of producing the desired spatial concentration profiles. The numerical and experimental flow patterns are very similar, showing banded RNA concentration profiles as required for high throughput transfection. The flow profile deviation with the simulation profile is most likely caused by a mismatch in the diffusion coefficient between experiments and simulations, the addition of circular coverslip that carries cell samples, and minor air bubbles trapped within of the channel. Creating similar RNA gradients in the orthogonal direction would double the number RNAs that one can test in a single experiment.

Fluid inlets can be used to load live neuronal cells with two gradients of distinct calcium indicators X-Rhod-1 and Fluo-4. Upon doing this, the distribution of these fluorophores are distributed and concentrated in the cytosol in a gradient dependent manner as expected. The next step is to stimulate the cells to assess the Ca++ response between cells that are positioned at different locations from the stimulus and have been loaded with differing amounts of the two calcium indicators.

Further studies flow multiple RNAs at user-defined concentrations into the chamber, transfecting the cells and assessing the translation and function of the transfected RNAs. The concentration of each individual RNA at any cell in the microfluidics chamber can be determined based upon the flow rates and initial RNA concentrations. The amount of each RNA that can diffuse into the cell can be determined based on the laser irradiation parameters. Measuring of the consequences of the RNA transfection and knowing the amounts of RNA that are introduced will permit a direct correlation between the RNAs that are introduced, their abundances, and the consequent cellular changes. This multigenic functional genomics assay is the high throughput TIPeR assay. While this can be done for cells in dispersed culture, it can also be performed for cells in a live tissue slice by positioning the slice in the chamber and flowing RNA over the tissue. The RNA concentration determination will require the added component of diffusion into the tissue but this can be modeled and then incorporated into the algorithms (COMSOL). To be able to rapidly change RNA identities for infusion into the TIPeR device, a purpose-built system attached to the chamber will use RNA capsules compatible with a positive-displacement infusion system. These capsules are low-volume containers (50 microliters to 1 mL) that can snap into a purpose-built positive-displacement pump without introducing contaminants; each capsule slot will be independently actuated and flow into a matching inlet on the device. Capsules containing species of RNA can be mixed-and-matched to fully customize cell loading and will be readily interchangeable with minimal down time.

The ability to manipulate and determine the amount of multiple RNAs that are transfected into multiple cells, all at differing concentrations, enable high throughput phenotypic analysis of the function of populations RNA.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A microfluidic device comprising:
   a first layer having a top and bottom surface, a thickness in-between, and a plurality of wells and a test chamber embedded in the top surface, each of the wells being fluidly connected to the test chamber by at least one microchannel, and a vacuum port embedded in the top surface fluidly connected to a vacuum channel extending to a position near the test chamber;

a second layer having a top and bottom surface, a thickness in-between, and a plurality of well openings, a vacuum port opening and a test chamber opening extending between the top and bottom surface, the test chamber opening being in alignment with the test chamber of the first layer, and an indentation embedded in the top surface forming a perimeter around the test chamber opening, the indentation comprising an aperture that extends through to the bottom surface of the second layer;

wherein the second layer is attachable to the top surface of the first layer such that each of the well openings of the second layer align with each of the wells of the first layer, the vacuum port opening of the second layer aligns with the vacuum port of the first layer, and the aperture of the second layer aligns with the vacuum channel of the first layer, and wherein the first and second layers are releasably interfaced.

2. The device of claim 1, further comprising a coverslip sized to cover the indentation and the test chamber opening of the second layer.

3. The device of claim 1, further comprising a third layer having a top and bottom surface, a thickness in-between, a plurality of well openings extending between the top and bottom surface, and a window opening extending between the top and bottom surface, wherein the third layer is attachable to the top surface of the third layer such that each of the well openings of the third layer align with each of the well openings of the second layer, and the window opening surrounds the indentation of the second layer.

4. The device of claim 1, further comprising a support layer attached to the bottom surface of the first layer.

5. The device of claim 1, wherein the first layer and the second layer each have at least two alignment slots that extend through top and bottom surfaces of each layer, each alignment slot being sized to accept a guide rod.

6. The device of claim 5, wherein the alignment slots are positioned such that passing the alignment slots of the second layer over guide rods inserted into the alignment slots of the first layer aligns each well opening of the second layer with each well of the first layer.

7. The device of claim 1, further comprising one or more bubble traps or degassing valves connected to the microchannels, the test chamber, or both, wherein the one or more bubble traps comprise an inner diameter greater than an inner diameter of each of the at least one microchannel.

8. The device of claim 1, further comprising one or more diffusor regions fluidly connecting two or more of the at least one microchannel, wherein the one or more diffusor regions are configured to combine fluid from the two or more microchannels to form a gradient of one or more agents that flow to the test chamber.

9. The device of claim 8, wherein the one or more agents comprise RNA.

10. The device of claim 9, further comprising one or more bubble traps in the at least one microchannel upstream from the test chamber.

11. A microfluidic device comprising:

a microchannel layer having a top surface, a bottom surface and a thickness in-between, the microchannel layer including:

a test chamber recessed into the top surface, the test chamber having a perimeter with a plurality of inlets and at least one outlet about the perimeter;

a plurality of inlet wells and at least one outlet well recessed into the top surface;

at least one vacuum port recessed into the top surface; and a plurality of microchannels recessed into the top surface, wherein at least one microchannel fluidly connects each of the plurality of inlet wells to a corresponding test chamber inlet of the plurality of inlets about the perimeter of the test chamber, at least one microchannel fluidly connects the at least one outlet well to the test chamber outlet, and at least one vacuum microchannel having a first end and a second end, with the first end being fluidly connected to the vacuum port and fluidly isolated from the test chamber;

a cover layer having a top surface, a bottom surface and a thickness in-between, the bottom surface of the cover layer being positioned on, and in contact with, the top surface of the microchannel layer, the cover layer further including:

a plurality of well openings passing through the top and bottom surfaces and aligned with each of the plurality of inlet wells of the microchannel layer;

a test chamber opening having a perimeter and passing through the top and bottom surfaces and aligned with the test chamber of the microchannel layer;

an indentation recessed into the top surface and positioned around the perimeter of the test chamber opening, wherein the indentation includes an aperture passing through the thickness to the bottom surface of the cover layer and is fluidly connected to the second end of the vacuum microchannel; and a coverslip having a perimeter edge, wherein the coverslip is sized such that the perimeter edge rests on the indentation and covers the test chamber opening and the indentation aperture.

* * * * *